United States Patent
Kavanagh et al.

(10) Patent No.: US 6,489,540 B1
(45) Date of Patent: Dec. 3, 2002

(54) PLASTID-TARGETING NUCLEIC ACID SEQUENCE, A NOVEL β-AMYLASE SEQUENCE, A STIMULUS-RESPONSIVE PROMOTER AND USES THEREOF

(75) Inventors: Thomas Anthony Kavanagh, Dublin (IE); Nga Thi Lao, Dublin (IE)

(73) Assignee: Advanced Technologies (Cambridge) Limited, London (GB)

( * ) Notice: Subject to any disclaimer, the term of this patent is extended or adjusted under 35 U.S.C. 154(b) by 0 days.

(21) Appl. No.: 09/375,140

(22) Filed: Aug. 16, 1999

(30) Foreign Application Priority Data

Aug. 19, 1998 (GB) .............................................. 9817959
Aug. 19, 1998 (GB) .............................................. 9817963
Mar. 24, 1999 (GB) .............................................. 9913014

(51) Int. Cl.$^7$ ........................ C12N 15/29; C12N 15/82; C12N 15/56; C12N 5/10; A01H 5/00; A01H 5/10; C12P 19/00

(52) U.S. Cl. ........................ 800/284; 800/287; 800/298; 800/317.2; 800/320.3; 800/320.1; 800/320; 800/317.4; 800/320.2; 800/317.3; 800/312; 435/70.1; 435/419; 435/430; 435/320.1; 435/252.3; 435/201; 536/23.6

(58) Field of Search .................................. 800/278, 284, 800/285, 287, 298, 317.2, 320, 320.3, 320.2, 320.1, 317.3, 317.4, 312; 435/468, 419, 410, 252.3, 70.1, 430, 320.1, 201; 536/23.6

(56) References Cited

U.S. PATENT DOCUMENTS 5,034,323 A 7/1991 Jorgensen et al.

FOREIGN PATENT DOCUMENTS

| GB | 9817959.1 | 8/1998 |
|---|---|---|
| GB | 9817963.3 | 8/1998 |
| GB | 9913014.8 | 3/1999 |
| WO | WO 90/11682 | 10/1990 |
| WO | WO 90/12084 | 10/1990 |
| WO | WO 91/19806 | 12/1991 |
| WO | WO 92/11382 | 7/1992 |
| WO | WO 92/22582 | 12/1992 |
| WO | WO 96/03513 | 2/1996 |
| WO | WO 97/16554 | 5/1997 |
| WO | WO 98/10081 | 3/1998 |

OTHER PUBLICATIONS

Lao, N. T. et al., "An Arabidopsis gene encoding a chloroplast–targeted B–amylase." 1999, The Plant Journal, vol. 20, pp. 519–527.*

Newman, T. et al., 1998a, GenBank Accession No. A1099858.*

Newman, T. et al., 1998a, GenBank Accession No. H37046.*

Bevan, M. et al., "Analysis of 1.9 Mb of contiguous sequence from chromosome 4 of *Arabidopsis thaliana*." 1998, Nature, vol. 391, pp. 485–488.*

Lazar, E. et al., Transforming Growth Factor a: Mutation of Aspartic Acid 47 and Leucine 48 Results in Different Biological Activities. 1988, Molecular and Cellular Biology, vol. 8, pp. 1247–1252.*

Bowie, J. U. et al., "Deciphering the Message in Protein Sequences: Tolerance to Amino Acid Substitutions." 1990, Science, vol. 247, pp. 1306–1310.*

Broun, P. et al., "Catalytic Plasticity of Fatty Acid Modification Enzymes Underlying Chemical Diversity of Plant Lipids." 1998, Science, vol. 282, pp. 1315–1317.*

Ainsworth et al., 1993, "Expression, Organisation and Structure of the Genes Encoding the waxy Protein (Granule–Bound Starch Synthase) in Wheat", Plant Mol. Biol. 22:67–82.

Baier and Dietz, 1997, "The Plant 2–Cys Peroxiredoxin BAS1 Is a Nuclear–Encoded Choloroplast Protein: Its Expressional Regulation, Phylogenetic Origin, and Implications for Its Specific Physiological Function in Plants", Plant J. 12:179–190.

Bevan, 1984, "Binary Agrobacterium Vectors for Plant Transformation", Nucl. Acids Res. 12:8711–8721.

Bevan et al., 1998, "Analysis of 1.9 Mb of Contiguous Sequence from Chromosome 4 of *Arabidopsis thaliana*", Nature 391:485–488.

Chan et al.,1994, "Novel Gene Expression System for Plant Cells Based on Induction of α–Amylase Promoter by Carbohydrate Starvation", J. Biol. Chem. 269:17635–17641.

Chen et al., 1994, "Expression of α–Amylases, Carbohydrate Metabolism, and Autophagy in Cultured Rice Cells Is Coordinately Regulated by Sugar Nutrient", Plant J. 6:625–636.

Daussant et al., 1981, "Cereal β–Amylase: Immunochemical Study on Two Enzyme–Deficient Inbred Lines of Rye", Planta 151:176–179.

Denyer et al.,1996, "The Elongation of Amylose and Amylopectin Chains in Isolated Starch Granules", Plant J. 10:1135–1143.

(List continued on next page.)

Primary Examiner—David T. Fox
Assistant Examiner—Anne Kubelik
(74) Attorney, Agent, or Firm—Pennie & Edmonds LLP

(57) ABSTRACT

The invention provides a novel chloroplast targeted novel β-amylase sequence (ct β-amylase), a novel chloroplast targeting nucleic acid sequence and a novel β-amylase sequence. There is also disclosed an inducible promoter which is independently stimulated by light or sugar stimulus. Methods of transforming plants using these sequences are described, as well as transformed plant cells, transformed plants and seed thereof, as well as chimaeric genes containing the sequences. Modification of starch levels in plants can be achieved, as well as the targeting of genes from the starch biosynthetic or degradative pathways, disease or pest resistance or variation of gene expression due to stimulus are described.

19 Claims, 10 Drawing Sheets

OTHER PUBLICATIONS

Duwenig et al., 1997, "Antisense Inhibition of Cytosolic Phosphorylase in Potato Plants (*Solanum tuberosum* L.) Affects Tuber Sprouting and Flower Formation with Only Little Impact on Carbohydrate Metabolism", Plant J. 12:323–333.

Eggermont et al., 1996, "High–Throughput RNA Extraction from Plant Samples Based on Homogenisation by Reciprocal Shaking in the Presence of a Mixture of Sand and Glass Beads", Plant Mol. Biol. Reporter 14:273–279.

Feinberg and Vogelstein, 1983, "A Technique for Radiolabeling DNA Restriction Endonuclease Fragments to High Specific Activity", Anal. Biochem. 132:6–13.

Hildebrand and Hymowitz, 1981, "Role of β–Amylase in Starch Metabolism during Soybean Seed Development and Germination", Physiol. Plant 53:429–434.

Horsch et al., 1985, "A Simple and General Method for Transferring Genes into Plants", Science 227:1229–1231.

Hylton et al., 1996, "The Effect of waxy Mutations on the Granule–Bound Starch Synthases of Barley and Maize Endosperms", Planta 198:230–237.

James et al., 1995, "Characterization of the Maize Gene sugary1, a Determinant of Starch Composition in Kernels", Plant Cell 7:417–429.

Jefferson et al., 1987, "GUS Fusions: β–Glucuronidase as a Sensitive and Versatile Gene Fusion Marker in Higher Plants", EMBO J. 6:3901–3907.

Kakefuda et al., 1986, "Chloroplast and Extrachloroplastic Starch–Degrading Enzymes in *Pisum sativum* L.", Planta 168:175–182.

Klösgen and Weil, 1991, "Subcellular Location and Expression Level of a Chimeric Protein Consisting of the Maize waxy Transit Peptide and the β–Glucuronidase of *Escherichia coli* in Transgenic Potato Plants", Mol. Gen. Genet. 225:297–304.

Li et al., 1992, "Characterization and Subcellular Localization of Debranching Enzyme and Endoamylase from Leaves of Sugar Beet", Plant Physiol. 98:1277–1284.

Liu et al., 1990, "Cis Regulatory Elements Directing Tuber––Specific and Sucrose–Inducible Expression of a Chimeric Class I Patatin Promoter/GUS–Gene Fusion", Mol. Gen. Genet.223:401–406.

Mita et al., 1995, "Sugar–Inducible Expression of a Gene for β–Amylase in *Arabidopsis thaliana*", Plant Physiol. 107:895–904.

Mita et al., 1997, "Mutants of *Arabidopsis thaliana* with Pleiotropic Effects on the Expression of the Gene for β–Amylase and on the Accumulation of Anthocyanin that Are Inducible by Sugars", Plant J. 1:841–851.

Mould and Gray, 1998, "Preparation of Chloroplasts for Protein Synthesis and Protein Import", In: *Cell Biology: A Laboratory Handbook*, Second Edition, vol. 2, Celis, ed., Academic Press, NY, pp. 81–86.

Mould and Gray, 1998, "Import of Nuclear–Encoded Proteins by Isolated Chloroplasts", In: *Cell Biology: A Laboratory Handbook*, Second Edition, vol. 2, Celis, ed., Academic Press, NY, pp. 286–292.

Nakamura et al., 1991, "Sucrose–Induced Accumulation of β–Amylase Occurs Concomitant with the Accumulation of Starch and Sporamin in Leaf–Petiole Cuttings of Sweet Potato", Plant Physiol. 96:902–909.

Newman et al., 1994, "Genes Galore: A Summary of Methods for Accessing Results from Large–Scale Partial Sequencing of Anonymous Arabidopsis cDNA Clones", Plant Physiol. 106:1241–1255.

Nielsen et al., 1997, "A β–Amylase in Potato Tubers Is Induced by Storage at Low Temperatures", Plant Physiol. 113:503–510.

Odell et al., 1985, "Identification of DNA Sequences Required for Activity of the Cauliflower Mosaic Virus 35S Promoter", Nature 313:810–812.

Peavey et al., 1977, "Characterization of Starch Breakdown in the Intact Spinach Chloroplast", Plant Physiol. 60:305–308.

Pwee and Gray, 1993, "The Pea Plastocyanin Promoter Directs Cell–Specific but not Full Light–Regulated Expression in Transgenic Tobacco Plants", Plant J. 3:437–449.

Rocha–Sosa et al., 1989, "Both Development and Metabolic Signals Activate the Promoter of a Class I Palatin Gene", EMBO J. 8:23–29.

Schatz and Dobberstin, 1996, "Common Principles of Protein Translocation Across Membranes", Science 271:1519–1526.

Schnell and Blobel, 1993, "Identification of Intermediates in the Pathway of Protein Import into Chloroplasts and Their Localization to Envelope Contact Sites", J. Cell Biol. 120:103–115.

Sonnewald et al., 1995, "A Second L–Type Isozyme of Potato Glucan Phosphorylase: Cloning, Antisense Inhibition and Expression Analysis", Plant Mol. Biol. 27:567–576.

Sweetlove et al., 1996, "Starch Metabolism in Tubers of Transgenic Potato (*Solanum tuberosum*) with Increased ADPglucose Phosphorylase", Biochem. J. 320:493–498.

Tetlow et al., 1994, "Starch Synthesis and Carbohydrate Oxidation in Amyloplasts from Developing Wheat Endosperm", Planta 194:454–460.

Thomson and Whatley, 1980, "Development of Nongreen Plastids", Ann. Rev. Plant Physiol. 31:375–394.

van Engelen et al., 1995, "pBINPLUS: An Improved Plant Transformation Vector Based on pBIN19", Transgenic Res. 4:288–290.

van der Leij et al., 1991, "Sequence of the Structural Gene for Granule–Bound Starch Synthase of Potato (*Solanum tuberosum* L.) and Evidence for a Single Point Deletion in the amf Allele", Mol. Gen. Genet. 228:240–248.

Wang et al., 1996, "Phytohormone–Regulated β–Amylase Gene Expression in Rice", Plant Mol. Biol. 31:975–982.

Wang et al., 1997, "Characterization of a Maize β–Amylase of cDNA Clone and Its Expression during Seed Germination", Plant Physiol. 113:403–409.

* cited by examiner

SEQUENCE LISTING

<160> NUMBER OF SEQ ID NOS: 11

<210> SEQ ID NO 1
<211> LENGTH: 294
<212> TYPE: DNA
<213> ORGANISM: Arabidopsis thaliana

<400> SEQUENCE: 1

| | | | | | |
|---|---|---|---|---|---|
| tcatttctca | tcataacaaa | gagagagaaa | aaaactatgg | aattgacact | gaattcctcg | 60 |
| agttctctta | tcaaacgtaa | agatgccaag | agttctagaa | accaagaaag | ttcctccaac | 120 |
| aacatgacct | ttgcgaagat | gaagccgcca | acatatcagt | tccaagcaaa | gaactcggtt | 180 |
| aaggaaatga | agttcactca | cgagaagacc | ttcacgccag | aaggtgaaac | ccttgagaaa | 240 |
| tgggagaagc | tccacgttct | ctcatatccca | cactccaaga | acgacgctag | cgtt | 294 |

<210> SEQ ID NO 2
<211> LENGTH: 1662
<212> TYPE: DNA
<213> ORGANISM: Arabidopsis thaliana

<400> SEQUENCE: 2

| | | | | | |
|---|---|---|---|---|---|
| gttccggtgt | tcgtcatgtt | accgctcgac | acagtaacaa | tgtcagggca | tttgaacaaa | 60 |
| ccacgagcca | tgaacgctag | tttgatggct | ctgaaaggag | ctggtgtgga | aggtgtgatg | 120 |
| gtggatgctt | ggtggggatt | ggtggagaaa | gatggaccta | tgaattataa | ctgggaaggc | 180 |
| tatgccgagc | ttatacagat | ggttcaaaag | cacggtctca | aactccaggt | cgttatgtca | 240 |
| ttccatcaat | gtggaggaaa | cgtaggagac | tcttgcagta | tccccttgcc | tccatgggtg | 300 |
| cttgaagaga | tcagcaagaa | ccctgatctt | gtctacacag | acaaatctgg | gagaaggaac | 360 |
| cctgaatata | tctccttggg | atgtgattct | gtgcctgtcc | taagaggaag | aacacctatc | 420 |
| caggtctact | cagatttcat | gaggagcttc | cgtgaacgat | ttgaaggcta | cataggagga | 480 |
| gttattgcgg | aaattcaagt | aggaatggga | ccttgtggag | aattgagata | cccatcatac | 540 |
| cctgaaagca | acgggacctg | gagattcccc | ggaattggag | agttccagtg | ctacgacaag | 600 |
| tatatgaaat | cgtcacttca | ggcatatgct | gaatcaattg | gaaaactaa | ctggggaaca | 660 |
| agcggacctc | atgatgccgg | cgagtacaag | aacctcccag | aagatactga | atttttcagg | 720 |
| agagacggaa | catggaatag | cgagtatgga | aagttttca | tggaatggta | ctccgggaag | 780 |
| ctgctagaac | atggagacca | actcctatct | tcagcgaaag | gtatctttca | aggaagcgga | 840 |
| gcaaagctat | caggaaaggt | agctggaatt | cactggcact | acaacaccag | gtcacacgca | 900 |
| gctgagctaa | ccgctggata | ttacaacaca | agaaaccatg | acgggtatct | gccaatagct | 960 |
| aagatgttca | acaaacatgg | agttgtgctc | aacttcacct | gcatggagat | gaaagacggg | 1020 |
| gagcaacctg | agcacgcgaa | ttgctcacca | gaaggtctgg | tcaagcaagt | acagaacgcg | 1080 |
| acaaggcagg | ccggaaccga | actagcaggg | gagaacgcgc | tagaacgata | tgactcgagc | 1140 |
| gcattcggac | aagtggtagc | aacaaatagg | tcagattctg | gaaatgggtt | aaccgcattt | 1200 |
| acttacctaa | gaatgaacaa | gcggttattt | gagggtcaaa | attggcagca | gttagtggag | 1260 |
| tttgttaaga | acatgaagga | aggtggtcat | gggaggagac | tctcaaaaga | agacacaact | 1320 |
| ggaagtgacc | tttatgttgg | atttgtcaaa | gcaagatcg | ctgagaatgt | ggaggaggct | 1380 |
| gctttagtgt | aatttcccac | ataggtacat | acatatagtg | tggtgtttat | tgtattcctg | 1440 |
| tctgataaat | aactagagag | atcaaaccag | taagagtgtt | aaagctatag | atttgcacaa | 1500 |

```
ttctgggtca gagtcagagc aaagagaagc aaaatcaaga tgatgtacac ttagatgtat    1560
cctatgagtt ttccttgtac atcatcttca tactcttaat ctcaaatact atgcattttt    1620
ctccaaaaaa aaaaaaaaaa gggcggccgc tctagaggat cc                       1662

<210> SEQ ID NO 3
<211> LENGTH: 1953
<212> TYPE: DNA
<213> ORGANISM: Arabidopsis thaliana

<400> SEQUENCE: 3
tcatttctca tcataacaaa gagagagaaa aaaactatgg aattgacact gaattcctcg      60
agttctctta tcaaacgtaa agatgccaag agttctagaa accaagaaag ttcctccaac     120
aacatgacct ttgcgaagat gaagccgcca acatatcagt tccaagcaaa gaactcggtt     180
aaggaaatga agttcactca cgagaagacc ttcacgccag aaggtgaaac ccttgagaaa     240
tgggagaagc tccacgttct ctcatacca cactccaaga acgacgctag cgttccggtg      300
ttcgtcatgt taccgctcga cacagtaaca atgtcagggc atttgaacaa accacgagcc     360
atgaacgcta gtttgatggc tctgaaagga gctggtgtgg aaggtgtgat ggtggatgct     420
tggtggggat tggtggagaa agatggacct atgaattata ctgggaagg ctatgccgag      480 cttatacaga tggttcaaaa gcacggtctc aaactccagg tcgttatgtc attccatcaa     540
tgtggaggaa acgtaggaga ctcttgcagt atccccttgc ctccatgggt gcttgaagag     600
atcagcaaga accctgatct tgtctacaca gacaaatctg ggagaaggaa ccctgaatat     660
atctccttgg gatgtgattc tgtgcctgtc ctaagaggaa gaacacctat ccaggtctac     720
tcagatttca tgaggagctt ccgtgaacga tttgaaggct acataggagg agttattgcg     780
gaaattcaag taggaatggg accttgtgga gaattgagat acccatcata ccctgaaagc     840
aacgggacct ggagattccc cggaattgga gagttccagt gctacgacaa gtatatgaaa     900
tcgtcacttc aggcatatgc tgaatcaatt gggaaaacta actggggaac aagcggacct     960
catgatgccg gcgagtacaa gaacctccca gaagatactg aattttttcag gagagacgga    1020 acatggaata gcgagtatgg aaagtttttc atggaatggt actccgggaa gctgctagaa    1080
catggagacc aactcctatc ttcagcgaaa ggtatctttc aaggaagcgg agcaaagcta    1140
tcaggaaagg tagctggaat tcactggcac tacaacacca ggtcacacgc agctgagcta    1200
accgctggat attacaacac aagaaaccat gacgggtatc tgccaatagc taagatgttc    1260
aacaaacatg gagttgtgct caacttcacc tgcatggaga tgaaagacgg ggagcaacct    1320
gagcacgcga attgctcacc agaaggtctg gtcaagcaag tacagaacgc gacaaggcag    1380
gccggaaccg aactagcagg ggagaacgcg ctagaacgat atgactcgag cgcattcgga    1440
caagtggtag caacaaatag gtcagattct ggaaatgggt taaccgcatt tacttaccta    1500
agaatgaaca agcggttatt tgagggtcaa aattggcagc agttagtgga gtttgttaag    1560
aacatgaagg aaggtggtca tgggaggaga ctctcaaaag aagacacaac tggaagtgac    1620
ctttatgttg gatttgtcaa aggcaagatc gctgagaatg tggaggaggc tgctttagtg    1680
taatttccca cataggtaca tacatatagt gtggtgttta ttgtattcct gtctgataaa    1740
taactagaga gatcaaacca gtaagagtgt taaagctata gatttgcaca attctgggtc    1800
agagtcagag caaagagaag caaaatcaag atgatgtaca cttagatgta tcctatgagt    1860
tttccttgta catcatcttc atactcttaa tctcaaatac tatgcatttt tctccaaaaa    1920
```

```
aaaaaaaaaa agggcggccg ctctagagga tcc                                   1953

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
aattcctcga gttctcttat c                                                  21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
ggggatccct gacattgtta c                                                  21

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 6
gctggtactc ctgcaggatc cggtccggaa ttccc                                   35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 7
gggaattccg gaccggatcc tgcaggcgta ccagc                                   35

<210> SEQ ID NO 8
<211> LENGTH: 1652
<212> TYPE: DNA
<213> ORGANISM: Arabidopsis thaliana

<400> SEQUENCE: 8
aagcttgtgt ctatttcaaa ttcttgaccg tagatgtcac aacatgcata tatcattgaa         60
aacagagcaa cacaggaaac caagcatatg tatctagata tacttagcaa gacataacta        120
tagtctttga atcaacatag ggattaatga tagagaatga ggaagctcaa gatttttatac       180 tcagtttctt acaaaacaaa tttctctcta actgcaaaaa caccaattag gatttgaaga       240
gcgtacctgt ttgagtcaat gtccaatgtc gtcccccgc cttctacatt tcttagcctg        300
ctgaataaaa gcacaagcca aaatgagaag gtgccaaagg cgataaggat caatttctac       360
cattcaaaaa actaatggtg agaattagaa acgagagaaa actacttgtt gaggaaatag       420
ccaaaagcgc aatcttcgtc acctgaataa agaccaaacc gtcactttca atgagtcagc       480
aagaaaaaga gagagagaga gagagagatt ctctataaca tttgagtcga catggattct       540
aatgcatcaa aagtcatctc caataaacaa acacttgaaa ctcacatggc taatagaaca       600
agatcaaagc ttaagtatt aagcattaca gacactactg gctaactttt gacacatgtt        660
```

-continued

```
cttaagtaac atagtatcaa tatccgtgaa tcacatcgaa cacacacaac aagggcttaa      720
tgcatcaaag tcctgttatt tccatataac aacatatttc atttacaaac agaatgcagc      780
attcaggcag tccaaatgga aaggttgaca aaaaaatata atcttgtaac tctacatata      840
tggcagaatg taataaccag gcaagaaaaa aacagaataa acagatcaat gagtatgata      900
taaaaaaaag tcacaaagaa tgtgccacag tgaacaagag ggccatgaga agaaattttc      960
aaagaaaata ttagcattgt tagaattttt tgggtcaatg gatctgtcag ctgcttagtt     1020
ggaaaacaca aatcttacag gaaggaaagt ccaagaaaaa gaaaataagc aaagttaata     1080
gccaccacaa gaaatttcat acagaaataa ttaaatcgtt gcacttatct tcttattcaa     1140
actaaaatca agagaactta ataatttca gccacgacga ccatgtgttc aaagccaaag     1200
gtgagaagcc aaaattatca gcttatctcc attaacaagg aaaagcaag actagattta     1260 agagttctct gtaactaaaa actgcaggag tgagtaagta aataattcac caacaggaaa     1320
acaaaactca attatctata gctgaataca catgtaaatg agaatttatt aactaaaaca     1380
tcttcctttg taactgatgt gacatttaca attttttcatt ttgaggtgta agaaccgtgt     1440
gacaagtgaa aaggttaaaa taagcaacct ttgtgatatt ttctctccac tttttgaaat     1500
tgggtctcca aaccacagcc aatcaatatt ctttataaat acaaacacac aaacagcatc     1560
tttctctcaa acacaaacat atcttctatc aaacaccaac agctctattc tctacctcat     1620
ttctcatcat aacaaagaga gagaaaaaaa ct                                    1652
```

<210> SEQ ID NO 9
<211> LENGTH: 86
<212> TYPE: PRT
<213> ORGANISM: Arabidopsis thaliana

<400> SEQUENCE: 9

```
Met Glu Leu Thr Leu Asn Ser Ser Ser Leu Ile Lys Arg Lys Asp
 1               5                  10                  15

Ala Lys Ser Ser Arg Asn Gln Glu Ser Ser Ser Asn Asn Met Thr Phe
                20                  25                  30

Ala Lys Met Lys Pro Pro Thr Tyr Gln Phe Gln Ala Lys Asn Ser Val
            35                  40                  45

Lys Glu Met Lys Phe Thr His Glu Lys Thr Phe Thr Pro Glu Gly Glu
        50                  55                  60

Thr Leu Glu Lys Trp Glu Lys Leu His Val Leu Ser Tyr Pro His Ser
    65                  70                  75                  80

Lys Asn Asp Ala Ser Val
                85
```

<210> SEQ ID NO 10
<211> LENGTH: 463
<212> TYPE: PRT
<213> ORGANISM: Arabidopsis thaliana

<400> SEQUENCE: 10

```
Val Pro Val Phe Val Met Leu Pro Leu Asp Thr Val Thr Met Ser Gly
 1               5                  10                  15

His Leu Asn Lys Pro Arg Ala Met Asn Ala Ser Leu Met Ala Leu Lys
                20                  25                  30

Gly Ala Gly Val Glu Gly Val Met Val Asp Ala Trp Trp Gly Leu Val
            35                  40                  45

Glu Lys Asp Gly Pro Met Asn Tyr Asn Trp Glu Gly Tyr Ala Glu Leu
```

```
             50                  55                  60
Ile Gln Met Val Gln Lys His Gly Leu Lys Leu Gln Val Val Met Ser
65                  70                  75                  80

Phe His Gln Cys Gly Gly Asn Val Gly Asp Ser Cys Ser Ile Pro Leu
                85                  90                  95

Pro Pro Trp Val Leu Glu Glu Ile Ser Lys Asn Pro Asp Leu Val Tyr
            100                 105                 110

Thr Asp Lys Ser Gly Arg Arg Asn Pro Glu Tyr Ile Ser Leu Gly Cys
            115                 120                 125

Asp Ser Val Pro Val Leu Arg Gly Arg Thr Pro Ile Gln Val Tyr Ser
        130                 135                 140

Asp Phe Met Arg Ser Phe Arg Glu Arg Phe Glu Gly Tyr Ile Gly Gly
145                 150                 155                 160

Val Ile Ala Glu Ile Gln Val Gly Met Gly Pro Cys Gly Glu Leu Arg
                165                 170                 175

Tyr Pro Ser Tyr Pro Glu Ser Asn Gly Thr Trp Arg Phe Pro Gly Ile
            180                 185                 190

Gly Glu Phe Gln Cys Tyr Asp Lys Tyr Met Lys Ser Ser Leu Gln Ala
            195                 200                 205

Tyr Ala Glu Ser Ile Gly Lys Thr Asn Trp Gly Thr Ser Gly Pro His
        210                 215                 220

Asp Ala Gly Glu Tyr Lys Asn Leu Pro Glu Asp Thr Glu Phe Phe Arg
225                 230                 235                 240

Arg Asp Gly Thr Trp Asn Ser Glu Tyr Gly Lys Phe Phe Met Glu Trp
                245                 250                 255

Tyr Ser Gly Lys Leu Leu Glu His Gly Asp Gln Leu Leu Ser Ser Ala
            260                 265                 270

Lys Gly Ile Phe Gln Gly Ser Gly Ala Lys Leu Ser Gly Lys Val Ala
            275                 280                 285

Gly Ile His Trp His Tyr Asn Thr Arg Ser His Ala Ala Glu Leu Thr
        290                 295                 300

Ala Gly Tyr Tyr Asn Thr Arg Asn His Asp Gly Tyr Leu Pro Ile Ala
305                 310                 315                 320

Lys Met Phe Asn Lys His Gly Val Val Leu Asn Phe Thr Cys Met Glu
                325                 330                 335

Met Lys Asp Gly Glu Gln Pro Glu His Ala Asn Cys Ser Pro Glu Gly
            340                 345                 350

Leu Val Lys Gln Val Gln Asn Ala Thr Arg Gln Ala Gly Thr Glu Leu
            355                 360                 365

Ala Gly Glu Asn Ala Leu Glu Arg Tyr Asp Ser Ser Ala Phe Gly Gln
        370                 375                 380

Val Val Ala Thr Asn Arg Ser Asp Ser Gly Asn Gly Leu Thr Ala Phe
385                 390                 395                 400

Thr Tyr Leu Arg Met Asn Lys Arg Leu Phe Glu Gly Gln Asn Trp Gln
                405                 410                 415

Gln Leu Val Glu Phe Val Lys Asn Met Lys Glu Gly Gly His Gly Arg
            420                 425                 430

Arg Leu Ser Lys Glu Asp Thr Thr Gly Ser Asp Leu Tyr Val Gly Phe
            435                 440                 445

Val Lys Gly Lys Ile Ala Glu Asn Val Glu Glu Ala Ala Leu Val
        450                 455                 460
```

<210> SEQ ID NO 11

-continued

```
<211> LENGTH: 548
<212> TYPE: PRT
<213> ORGANISM: Arabidopsis thaliana

<400> SEQUENCE: 11

Met Glu Leu Thr Leu Asn Ser Ser Ser Leu Ile Lys Arg Lys Asp
 1               5                  10                  15

Ala Lys Ser Ser Arg Asn Gln Glu Ser Ser Asn Asn Met Thr Phe
                20                  25                  30

Ala Lys Met Lys Pro Pro Thr Tyr Gln Phe Gln Ala Lys Asn Ser Val
            35                  40                  45

Lys Glu Met Lys Phe Thr His Glu Lys Thr Phe Thr Pro Glu Gly Glu
        50                  55                  60

Thr Leu Glu Lys Trp Glu Lys Leu His Val Leu Ser Tyr Pro His Ser
65                  70                  75                  80

Lys Asn Asp Ala Ser Val Pro Val Phe Val Met Leu Pro Leu Asp Thr
                85                  90                  95

Val Thr Met Ser Gly His Leu Asn Lys Pro Arg Ala Met Asn Ala Ser
               100                 105                 110

Leu Met Ala Leu Lys Gly Ala Gly Val Glu Gly Val Met Val Asp Ala
           115                 120                 125

Trp Trp Gly Leu Val Glu Lys Asp Gly Pro Met Asn Tyr Asn Trp Glu
130                 135                 140

Gly Tyr Ala Glu Leu Ile Gln Met Val Gln Lys His Gly Leu Lys Leu
145                 150                 155                 160

Gln Val Val Met Ser Phe His Gln Cys Gly Gly Asn Val Gly Asp Ser
                165                 170                 175

Cys Ser Ile Pro Leu Pro Pro Trp Val Leu Glu Glu Ile Ser Lys Asn
            180                 185                 190

Pro Asp Leu Val Tyr Thr Asp Lys Ser Gly Arg Arg Asn Pro Glu Tyr
        195                 200                 205

Ile Ser Leu Gly Cys Asp Ser Val Pro Val Leu Arg Gly Arg Thr Pro
    210                 215                 220

Ile Gln Val Tyr Ser Asp Phe Met Arg Ser Phe Arg Glu Arg Phe Glu
225                 230                 235                 240

Gly Tyr Ile Gly Gly Val Ile Ala Glu Ile Gln Val Gly Met Gly Pro
                245                 250                 255

Cys Gly Glu Leu Arg Tyr Pro Ser Tyr Pro Glu Ser Asn Gly Thr Trp
            260                 265                 270

Arg Phe Pro Gly Ile Gly Glu Phe Gln Cys Tyr Asp Lys Tyr Met Lys
        275                 280                 285

Ser Ser Leu Gln Ala Tyr Ala Glu Ser Ile Gly Lys Thr Asn Trp Gly
    290                 295                 300

Thr Ser Gly Pro His Asp Ala Gly Glu Tyr Lys Asn Leu Pro Glu Asp
305                 310                 315                 320

Thr Glu Phe Phe Arg Arg Asp Gly Thr Trp Asn Ser Glu Tyr Gly Lys
                325                 330                 335

Phe Phe Met Glu Trp Tyr Ser Gly Lys Leu Leu Glu His Gly Asp Gln
            340                 345                 350

Leu Leu Ser Ser Ala Lys Gly Ile Phe Gln Gly Ser Gly Ala Lys Leu
        355                 360                 365

Ser Gly Lys Val Ala Gly Ile His Trp His Tyr Asn Thr Arg Ser His
    370                 375                 380

Ala Ala Glu Leu Thr Ala Gly Tyr Tyr Asn Thr Arg Asn His Asp Gly
```

-continued

```
385                 390                 395                 400
Tyr Leu Pro Ile Ala Lys Met Phe Asn Lys His Gly Val Val Leu Asn
            405                 410                 415

Phe Thr Cys Met Glu Met Lys Asp Gly Glu Gln Pro Glu His Ala Asn
            420                 425                 430

Cys Ser Pro Glu Gly Leu Val Lys Gln Val Gln Asn Ala Thr Arg Gln
            435                 440                 445

Ala Gly Thr Glu Leu Ala Gly Glu Asn Ala Leu Glu Arg Tyr Asp Ser
    450                 455                 460

Ser Ala Phe Gly Gln Val Val Ala Thr Asn Arg Ser Asp Ser Gly Asn
465                 470                 475                 480

Gly Leu Thr Ala Phe Thr Tyr Leu Arg Met Asn Lys Arg Leu Phe Glu
            485                 490                 495

Gly Gln Asn Trp Gln Gln Leu Val Glu Phe Val Lys Asn Met Lys Glu
            500                 505                 510

Gly Gly His Gly Arg Arg Leu Ser Lys Glu Asp Thr Thr Gly Ser Asp
        515                 520                 525

Leu Tyr Val Gly Phe Val Lys Gly Lys Ile Ala Glu Asn Val Glu Glu
    530                 535                 540

Ala Ala Leu Val
545
```

PLASTID-TARGETING NUCLEIC ACID SEQUENCE, A NOVEL β-AMYLASE SEQUENCE, A STIMULUS-RESPONSIVE PROMOTER AND USES THEREOF

The precise mechanisms by which starch is synthesised and degraded in plants are unknown, despite the isolation and characterisation of a number of enzymes that are presumed to be involved in the process.

Starch is accumulated in the chloroplasts of leaves during the day and is used to supply the needs of the plant for energy and biosynthesis during the night. The mode by which this so-called transient starch is mobilised is not fully understood, but must involve the co-ordinated regulation of synthetic and degradative enzyme activities. In leaf tissues the main degradation pathway is thought to involve phosphorolytic and hydrolytic activities, especially α-glucosidase (E.C. 3.2.1.3) (Nielson and Stitt, 1997).

Starch is also accumulated in the amyloplasts in storage organs such as seeds, fruit and tubers. In this case starch is stored over longer periods of time and mobilisation of the starch is accompanied by degeneration of the storage organ tissues and increases in amylolytic and phosphorolytic activities. However, there is evidence to suggest that turnover of starch is also occurring in the amyloplasts of the storage organ (Sweetlove et al, 1996). This again requires the co-ordinated regulation of the synthetic and degradative enzyme activities.

Chloroplasts and amyloplasts are both derived from proplastids and therefore have many characteristics in common besides being the site of starch synthesis in leaves and storage organs respectively; chloroplasts can be converted to amyloplasts and other types of plastid (Thomson and Whatley, 1980).

Starch is a mixture of two polysaccharides: amylose which is a linear chain of glucosyl units linked by α-1,4-glycosidic bonds; and amylopectin which is made up of many linear chains of α-1,4-polyglucans which are joined together by α-1,6 glycosidic bonds.

Enzymes involved in the synthesis of starch are ADPG pyrophosphorylase (E.C. 2.7.7.21), starch synthase (E.C. 2.4.1.21) and branching enzyme (E.C. 2.4.1.18). ADPG pyrophosphorylase is responsible for supplying the substrate ADPG, this molecule serving as the donor of glucose monomers which are linked together by the concerted action of starch synthases (α-1,4 bonds) and branching enzymes (α-1,6 bonds).

It is thought that the insoluble, crystalline structure of starch grains is formed by the close packing of the extended helical, branched amylopectin molecules, with the linear amylose molecules filling any spaces.

A range of starch-degrading enzyme activities has been reported including α-amylase (E.C. 3.2.1.1), isoamylase (E.C. 3.2.1.68), β-amylase (E.C. 3.2.1.2), α-glucosidase (E.C. 3.2.1.3), starch phosphorylase (E.C. 2.4.1.1) and disproportionating enzyme (E.C. 2.4.1.25). Many of these enzyme activities exist in multiple forms in plants and some are thought to be involved in the synthesis of starch. All probably take part, to some extent, in the starch mobilisation process, however their exact roles and possible interactions are yet to be determined. The difficulties in attributing roles for the different enzymes is best exemplified by reference to two of the enzyme activities which are thought to. be the major contributors to starch breakdown in plants: starch phosphorylase and amylase.

Starch phosphorylase catalyses the reversible release of glucose-i-phosphate from α-1,4-glucans. Two forms of starch phosphorylase are found in plant tissues: Pho1, or the L-type, is located inside plastids and has a high affinity towards maltodextrins; Pho2, or the H-type, is cytosolic and has high affinity to large, highly branched polyglucans such as glycogen. Although the plastidic Pho1 enzyme would be a likely candidate to be involved in the mobilisation of starch, antisense inhibition of the leaf enzyme activity had no effect on the starch accumulation in leaves of transgenic potato plants (Sonnewald et al., 1995). In another study, antisense inhibition of the cytoplasmic Pho2 had an influence on the sprouting behaviour of transgenic potato tubers, but had no effect on the starch accumulation and degradation (Duwenig et al., 1997).

There are two major groups of amylase both of which hydrolyse α-1,4-glucosidic linkages in amylose and amylopectin: α-amylase acts randomly on non-terminal linkages, whereas β-amylase acts to release maltose units starting from the non-reducing end of the polyglucan chain. The subcellular location of α-amylase in the apoplastic space of plant cells is thought to reflect the fact that the enzyme is normally secreted. However, in a number of plants such as rice (Chen, et al., 1994) and sugar beet (Li, et al., 1992) the enzyme is also located inside chloroplasts and amyloplasts, despite the finding that the signal sequences at the amino-terminus of a number of α-amylase proteins are characteristic for translocation of protein across the ER membrane rather than the plastid membrane (Chen et al, 1994). In a study where the promoter and signal sequence of a rice α-amylase gene was fused to the bacterial GUS gene and introduced into rice, tobacco and potato using Agrobacterium-mediated transformation (Chan et al., 1994), it was demonstrated that the expressed GUS fusion protein was first transported to the endoplasmic reticulum and then exported into the culture medium of suspension cultures made from transgenic cells. It has been shown in a number of studies that α-amylase will degrade native starch molecules.

In contrast, in vitro studies have shown that β-amylase will not degrade native starch granules without prior digestion of the granule with other enzymes. Mutants of rye (Daussant et al., 1981) and soybean (Hildebrand and Hymowitz, 1981) that lack active β-amylase or contain only traces of activity, respectively, apparently show normal growth and development. In addition, transgenic Arabidopsis plants in which the levels Of β-amylase have been greatly reduced, do not show severe growth defects (Mita et al., 1997). Attempts to define the precise physiological role of β-amylases in plants have been hampered by inconclusive data concerning subcellular location. Although one study (Kakefuda et al., 1986) reported the presence of two, β-amylases in pea chloroplasts, most studies involving species such as *Vicia faba*, barley, wheat, soybean, sweet potato and pea have concluded that most, if not all, β-amylase activity is extrachloroplastic (Nakamura et al., 1991). This view is supported by the fact that all β-amylase genes cloned to date encode proteins that lack amino-terminal chloroplast transit peptide sequences.

In cereals, three types of β-amylase have been described: an endosperm-specific form that accumulates during caryopsis maturation; a form that is synthesised de novo in aleurone cells of rice and maize during germination (Wang et al., 1996; 1997); and a β-amylase which is ubiquitous in vegetative organs. In Arabidopsis, the ubiquitous form accounts for approximately 80% of the total starch-degrading activity of rosette leaves. In common with all other β-amylase genes cloned to date, the gene for the ubiquitous Arabidopsis β-amylase does not encode a protein with a subcellular targeting signal, thus the enzyme is likely to be located in the cytosol.

The findings from a number of studies that the degradative activities can be removed without an adverse effect on the viability of the plant, plus the subcellular location of starch degrading enzymes outside the plastid, is surprising. The apparent absence of a plastid-localised β-amylase activity is especially surprising in light of the fact that the expected major end-product of β-amylase activity, namely maltose, has been identified as a product of starch degradation in isolated chloroplasts (Peavey et al., 1977). More recently, it has been shown that both glucose and maltose are exported from isolated cauliflower bud amyloplasts during the process of starch mobilisation (Neuhaus et al., 1995).

The ability to manipulate the amount of starch in the plastids of leaves or storage organs would be of high benefit to various industrial processes which utilise plant starches. For example, in an attempt to increase the starch content of potato tubers, it has been shown previously that when *E. coli* ADPG PPase glgC16 is overexpressed in transgenic potato tubers, there is an increase in flux of carbon into starch but there is only a small increase in net accumulation of starch (Sweetlove et al., 1997). Analysis of enzyme activities in the overexpressing lines showed that, apart from the alteration in ADPG PPase, the activity of amylase, specifically β-amylase was also altered. This data suggests that the accumulation of starch in tubers overexpressing glgC16 protein is prevented by the breakdown of the newly synthesised starch, i.e. the starch is being turned over.

In another example, the availability of starch during the malting process is closely correlated with the types and amounts of degradative enzyme activities in the plant, specifically the storage organs. An increase in the degradative capacity of the crop would make the malting of cereal grain or the conversion of starch from tubers, or other storage organs, to alcohol more efficient and productive.

The type of starch present in the storage organ depends on the forms and activities of the ADPG pyrophosphorylase, starch synthase, branching enzyme and the degradative enzymes present. The interactions between the various enzymes will also be important.

There is considerable interest in creating novel starches in planta as this will reduce the costs of processing and modification of the starch before use in a variety of industries such as food, paper, pharmaceuticals, glue, oil and textiles. The following examples show how starch hydrolytic activity can be important in altering the structure of starch in vivo.

It has been shown that, in maize kernels, the sugaryl mutation causes the absence of a debranching enzyme which hydrolises α-1,6-glycosyl linkages of starch (James et al., 1995). The mutation results in the decreased concentration of amylopectin and accumulation of the highly branched glucopolysaccharide, phytoglycogen.

It has been shown that in pea, short oligosaccharide molecules, starting with maltose and adding successive glucose units up to maltoheptose, specifically stimulate the activity of granule bound starch synthase I (GBSSI) (Denyer et al., 1996) which is generally accepted to be the major enzyme responsible for the synthesis of amylose (e.g. van der Leij et al., 1991; Hylton et al., 1995; Ainsworth et al., 1993). The manipulation of GBSSI activity by controlling the supply of malto-oligosaccharides is the subject of a recent patent (WO 97/16554) and suggests that an increase in the concentration of malto-oligosaccharides, and thus an increase in the ratio of amylose to amylopectin in the starch, can be brought about by the introduction of degradative enzymes namely α-amylase, β-amylase, disproportionating enzyme, debranching enzyme and starch phosphorylase. Patent WO 97/16554 also states that genes for plastidial isoforms of these enzymes have been cloned. However, as discussed above, no β-amylase genes isolated to date encode a β-amylase enzyme with a protein targeting sequence and, in addition, there is doubt that α-amylases are originally targeted to plastids (Chen et al., 1994; Chan et al., 1994). Later in WO 97/16554, reference is made to the engineering of a suitable β-amylase CDNA sequence to add a plastid targeting sequence.

In addition to the industrial uses for starch in the storage organs, the amount of starch in the leaf has significant importance for the agronomy of a crop. Starch is synthesised in the leaf during daylight from the carbon fixed during photosynthesis. The starch is stored in the chloroplast and is broken down at night to become a source of energy and intermediates for metabolism in the plant. By which mechanisms the source-sink relationship is controlled are unknown at present, however, it is clear that manipulation of the amount and availability of the starch in leaf plastids will have a profound influence on plant productivity (biomass and yield).

The amount of starch in the leaf will also be important for those crops where the leaf is the major plant commodity, for example tobacco. It is known that starch content has an influence on the eventual flavour of tobacco when smoked. Provision of a means to manipulate the level of starch in tobacco leaves could be of interest to the tobacco industry.

We describe here, for the first time, the isolation of a cDNA encoding a novel β-amylase enzyme which is targeted to plastids (henceforth known as chloroplast targeted (ct) β-amylase), by a novel targeting sequence. The isolation of this entire coding sequence is surprising, as it has generally been thought that β-amylase would only take part in the hydrolysis of starch once smaller polyglucan fragments had been released, either by translocation or through breakdown of the membrane, from the plastid into the cytoplasm. Location of the enzyme in plastids opens up the unforeseen possibility that ct β-amylase is involved in the degradation of transient starch located in chloroplasts and storage starch located in amyloplasts.

The similarity of characteristics between chloroplasts and amyloplasts (Thomson and Whatley, 1980) is of relevance to the current invention, as it has been shown that the transit peptides from chloroplast-targeted polypeptides can import heterologous polypeptides into amyloplasts and vice versa. For example, the transit peptide from the maize granule bound starch synthase enzyme when fused to the *E. coli* β-glucuronidase (GUS) protein will import the GUS protein not only into amyloplasts but also into chloroplasts (Klosgen and Weil, 1991).

In addition, we show that expression of the ct-Bmy gene in Arabidopsis and the expression of ct-Bmy promoter:GUS fusions in transgenic tobacco can be regulated independently by both light and sucrose. This is surprising in view of the tightly coupled light and sugar induction responses of ATβ-Amy of Arabidopsis (Mita et al, 1995).

The present invention provides a nucleic acid sequence known herein as SEQ. ID. No. 1 and being from 1–294 nucleotides and having therewithin a sequence capable of targeting a further coding sequence to a plant plastid, or sequences being at least 65% or more homologous with the disclosed sequence SEQ. ID. No. 1 and having the same targeting ability.

Preferably the nucleic acid sequence encodes about 94 and more preferably about 85 amino acid residues.

The present invention also provides a nucleic acid sequence known herein as SEQ. ID. No. 2 and being from 1–1642 nucleotides and having therewithin a sequence capable of encoding β-amylase, or sequences being at least 65% or more homologous with the disclosed sequence within SEQ. ID. No. 2 and having the same encoding ability.

The present invention also provides a nucleic acid sequence known herein as SEQ. ID. No. 3 and being from 1–1953 nucleotides and having therewithin a sequence capable of encoding chloroplast targeted β-amylase, or sequences being at least 65% or more homologous with the disclosed sequence within SEQ. ID. No. 3 and having the same encoding ability.

Homologous sequences also include those sequences which hybridise to SEQ. ID. No. 1, SEQ. ID. No. 2 or SEQ. ID. No. 3 under medium stringency conditions (washing at 2×SSC at 65° C.).

Preferably the nucleic acid sequence is an mRNA or cDNA sequence, although it may be genomic DNA.

The present invention also provides a method of increasing or decreasing in a plant the activity of an enzyme in the pathway of starch biosynthesis or degradation, the method comprising the steps of stably incorporating into a plant genome a chimaeric gene comprising a nucleic acid sequence encoding a plastid targeting sequence and a coding sequence for an enzyme in the starch biosynthetic or degradative pathway, and regenerating a plant having an altered genome.

The present invention also provides a method of targeting proteins or enzymes to a plant plastid, the method comprising the steps of stably incorporating into a plant genome a chimaeric gene comprising a nucleic acid sequence encoding a plastid targeting sequence and a coding sequence for a protein or an enzyme, and regenerating a plant having an altered genome, the protein or enzyme being one or more in the pathway of the following group: lipid synthesis, photosynthesis, amino acid metabolism, nitrogen fixation, carbon fixation or synthesis of carbohydrate polymers; or being able to confer a characteristic to the plant, the characteristic being selected from one or more of the following group: herbicide resistance and pest resistance, for example, including fungal, bacterial or viral resistance.

The present invention also provides plants having therein a chimaeric gene comprising a promoter, a nucleic acid coding sequence encoding the plastid targeting sequence, the sequence being capable of targeting a coding sequence of an enzyme in the starch biosynthetic or degradative pathway to a plant plastid, and a terminator.

The present invention further provides a nucleic acid sequence capable of directing expression of a product encoded by a coding sequence which is operably linked thereto, said nucleic acid sequence being known herein as SEQ.ID. No. 8, or being at least 65% homologous therewith and having substantially the same function thereas, and said nucleic acid sequence being responsive to stimulus, the level of expression of said product being variable in response to the stimulus applied to said nucleic acid sequence.

The present invention further provides a method of varying the level of expression of a product encoded by a coding sequence operably linked to a nucleic acid sequence capable of directing expression of said product in a plant, said method comprising the steps of stably incorporating into a plant genome a chimaeric gene comprising a nucleic acid sequence capable of directing expression of a product encoded by a coding sequence that is operably linked thereto, said nucleic acid sequence having substantially the sequence of SEQ.ID. No. 8 or being at least 65% homologous therewith and having substantially the same function thereas, and being responsive to stimulus.

Preferably the stimulus is the presence or absence of light and/or varying levels of sugar. Alternatively the stimulus is a stimulus which is developmentally controlled.

Advantageously the sugar is one or more of sucrose or glucose.

Preferably the sugar is sucrose.

Advantageously the inducible promoter, or nucleic acid sequence capable of directing expression of said product in a plant, is operable under conditions when there is no light but sugar is present, or when there is no sugar but light is present. The tissue of a plant where no light but sugar is present may suitably be underground organs or sink organs. Underground organs may be, for example, tubers, rhizomes or roots, whereas other sink organs may be young leaves or seeds.

The tissue of a plant where no sugar but light is present may be older leaves (where no sugar is transported), flower parts or germinating seeds.

Constructs and chimaeric genes having the DNA structural features described above are also aspects of the invention.

Plant cells containing a chimaeric gene comprising a nucleic acid sequence encoding a plastid targeting sequence hereinabove described and a nucleic acid coding sequence of an enzyme in the starch biosynthetic or degradative pathway, or a chimaeric gene comprising a nucleic acid sequence capable of directing expression of a further coding sequence, or a chimaeric gene comprising a nucleic acid sequence hereinabove. described that is responsive to stimulus and a coding sequence, the level of expression of said coding sequence being variable in response to the stimulus applied to said nucleic acid sequence are also an aspect of this invention, as is the seed of the transformed plant containing one or more chimaeric genes according to the invention.

Advantageously the plastid targeting sequence is the sequence SEQ. ID. No. 1.

In a first aspect of the invention the above method may be used to alter the metabolism of a leaf such that starch is accumulated therein or mobilised therefrom, this process altering the source-sink relationships within the plant as a whole. Such may be achieved by providing the targeting sequence and a nucleic acid coding sequence of an enzyme in the starch biosynthesis or degradative pathway under the direction of a suitable promoter. Suitable promoter selection would result in plants with increased or decreased levels of starch in the leaves which might be useful, for example, in the tobacco industry; or alternatively would result in changes in yield of starch in various other plant tissues such as tubers, fruit and roots following modification of the source-sink relationships of the plant.

In this embodiment of the invention a suitable promoter would direct expression of the plastid targeting sequence and the coding sequence of an enzyme in the starch biosynthetic or degradative pathway throughout the whole plant, so called constitutive expression, or specifically to the leaves. These changes will have a profound effect such that the starch content and/or the yield of the organs of the plant would be significantly altered.

A preferred promoter capable of directing expression throughout all plant tissues is the full or truncated promoter taken from cauliflower mosaic virus 35S gene. For storage organ expression, preferred promoters can be taken from the high molecular weight glutenin gene, the α, β-gliadin gene, the hordein gene and the patatin gene. For leaf expression, preferred promoters can be taken from the gene for the small subunit of ribulose bisphosphate carboxylase or the pea plastocyanin gene. One skilled in the art will recognise other suitable promoters, for example the nopaline synthase promoter for constitutive expression and the chlorophyll a/b binding protein promoter for specific leaf expression.

The coding sequence, or parts thereof, for the enzyme in the starch biosynthetic or degradative pathway may be arranged in the normal reading frame direction, i.e. sense, or in the reverse reading frame direction, i.e. antisense. Up or down regulation of the activity of the enzyme in a plant using sense, antisense or cosuppression technology (the latter as described by DNAP in their European Patents Nos. 0465572 and 0647715) may be used to achieve alteration in the starch of the plant.

In a second aspect of the invention the inventive method may also be used to alter the metabolism of starch in storage organs such that starch content is increased and/or the starch is provided in a suitable form as required for the purposes of particular industrial processes. Such processes including paper making; manufacture of pharmaceuticals, textiles, dyes and building products; provision of baking, dairy and snack food products; making canned, dried or instant foods; malting of grain and production of syrups and alcohol.

In the first or second aspect of the method the enzyme selected for use in the chimaeric gene of the methods may be one from the starch degradative pathway, i.e. a starch degrading enzyme. Advantageously, the chimaeric gene comprises a chloroplast targeted β-amylase (hereinafter known as ct β-amylase), and more preferably comprises ct β-amylase derived from *Arabidopsis thaliana,* (hereinafter known as At ct β-amylase), see SEQ. ID. No. 3. Sequences homologous to At ct β-amylase which may be derivable from other plant sources such as potato, tobacco, wheat, maize and barley may also be used. Standard methods of cloning by hybridisation or polymerase chain reaction (PCR) techniques may be used to isolate sequences from such organisms: for example molecular cloning techniques such as those described by Sambrook et al. (1989) and the PCR techniques described by Innes et al. (1990). Other starch degrading enzymes, the coding sequence of one or more of which would be suitable for use with the plastid targeting sequence, include α-amylase, disproportionating enzyme, debranching enzyme, starch phosphorylase, α-glucosidase and non-plastidic β-amylase.

In the second aspect of the inventive method preferred promoters which would direct expression to the storage organs of plants could be selected, for example, from the genes from the following list: the gene for high molecular weight glutenin of wheat endosperm; the gene for α,β-gliadin of wheat endosperm; the hordein gene of barley endosperm; or the gene for patatin from potato tubers. Other suitable promoters are known to those skilled in the art.

In either aspect of the invention, the alteration of tissue metabolism or alteration of starch type or characteristics may be made stimulus responsive, i.e. inducible, by virtue of use of the inducible promoter described herein (SEQ. ID. No. 8). For example, the light inducibility aspect of the inducible promoter could be used to manipulate seed set by inducing a gene such as Barnase (as exemplified in Patent WO 98/10081) to affect pollen development, or to affect non-light responsive genes in otherwise light-dependant processes such as fruit ripening or seed germination. The light inducible promoter could also be used to turn on genes which affect secondary metabolite production in leaves, for example alkaloid production. Light inducible promoters may also be used to manipulate starch biosynthetic enzyme genes in leaves or other photosynthetic tissue, or for example in turning on genes after removal of tubers, for example, from storage in darkness. The sugar-inducibility aspect of the inducible promoter could be used to regulate genes in, for example, developing tuber or other non-photosynthetic tissue such as genes for pest resistance and/or genes which might affect the quality of the post-harvest crop. For potatoes, resistance genes to blight, blackleg and dry rot would be particularly of benefit and could be most advantageously cloned into recombinant genes with sugar inducible promoters. Alternatively, the sugar inducibility aspect of the inducible promoter could be used to drive the expression of genes for selectable markers in the tissue culture process.

One skilled in the art can readily delineate the sugar inducible responsive element from SEQ. ID. No. 8 and/or the light inducible responsive element by using well known techniques, such as deletion studies. Pwee and Gray (1993) describe such a deletion study within the pea plastocyanin gene using a marker gene in order to determine operative regions thereof.

Methods described herein or in, for example, laboratory manuals by Sambrook et al (1989) and Gelvin and Stanton (1995) for cloning gene sequences and inserting them into appropriate carriers (vectors or plasmids etc.) are techniques well known to the skilled man for putting such concepts into effect. The chimaeric gene or genes as described above may be introduced on their own, or be accompanied by one or more other chimaeric genes, such as one or more of the other genes described above. In the case of the above described embodiments utilising a first chimaeric gene encoding an enzyme of the starch degradative pathway, the second chimaeric gene may, for example, comprise a nucleic acid sequence encoding an enzyme from the starch biosynthetic pathway also under the direction of a suitable promoter and a suitable terminator. The promoter and/or terminator of the second chimaeric gene may be the same as or different from the promoter and/or terminator of the first chimaeric gene. Suitable sequences encoding enzymes from the starch biosynthetic pathway are the nucleic acid sequences for sucrose synthase, ADPG pyrophosphorylase, starch synthase, and may also include branching enzyme, α-amylase, isoamylase, non-plastidic β-amylase, α-glucosidase, starch phosphorylase and disproportionating enzyme.

Methods for the introduction of more than one chimaeric gene into a plant have been described and comprise the construction of a binary vector with the chimaeric genes joined together in one nucleic acid molecule; cotransformation using two or more different Agrobacterium cells, for example, with different binary vectors containing different chimaeric genes therein; or the transformation of a plant which already has a chimaeric gene with a second, different chimaeric gene, i.e. retransformation. In the latter case, the method of selection of transgenic plants after the introduction of the second chimaeric gene must be different from the selection method used for the introduction of the first chimaeric gene. Suitable selectable markers would include those for hygromycin, kanamycin, sulphonamide and Basta resistance. Biological methods such as crossing two plants, each plant containing a single chimaeric gene can also be used.

Use of two chimaeric gene constructs could be made in order to alter the starch content of an already transformed plant which shows a significant increase in a first enzyme activity and a consequent change in the synthesis of starch.

Thus, the present invention further provides a method of altering in a transgenic plant, which plant already shows an increase or decrease in an enzyme activity as a result of genetic transformation, a further enzyme in order to up or down regulate said further enzyme and thereby increase or decrease the amount of starch produced by the retransformed plant.

Advantageously the first transformed plant is a plant having an increased enzyme activity in the starch biosynthetic pathway. An example of an attempt to increase the starch content of a plant is a transgenic potato transformed with the gene for ADPG-PPase, for example glgC16 (see for example, WO 91/19806). The amount of starch increase in such a plant has been relatively small. This first transformed plant is advantageously retransformed with a chimaeric gene for a starch degrading enzyme, suitably comprising, for example, At ct β-amylase. The glgC16 protein is expressed in the first transformed tubers and results in increased ADPG-PPase activity and an increase in flux of carbon to starch. Advantageously, the expression of the chimaeric At ct β-amylase gene, or parts thereof, in the retransformed tubers results in down regulation of the ct β-amylase activity, i.e. cosuppression or antisense technology, thus providing for an increase in starch accumulation.

Preferably the expression of the second enzyme is directed to tubers. A suitable promoter to direct the expression of the At ct β-amylase chimaeric gene in tubers is the promoter from the gene for patatin.

The first transformed potato plant expressing glgC16 is kanamycin resistant, therefore the binary vector construct for the At ct β-amylase chimaeric gene carries a different resistance gene, suitably a gene for sulphonamide resistance, for example. Increased starch production in the potato tuber would be of benefit, for example, to the potato crisp manufacturer as a 1% increase in potato dry matter would result in a 4% increase in product.

Potato crisp manufacture also serves to illustrate another benefit of the invention. When potato tubers are stored at temperatures below 8° C., reducing sugars, glucose and fructose from the breakdown of starch accumulate. When the potatoes are fried for crisps the reducing sugars react with amino acid in the Maillard reaction to give rise to brown colouration and off-tastes in the product. Introduction into potato plants of a chimaeric gene which would stop the breakdown of starch and thus the accumulation of reducing sugars would be of benefit to the snack food industry. Preferably the chimaeric gene would comprise the coding sequence, or a part of the sequence, for ct β-amylase in a cosuppression or antisense construct, driven by a suitable promoter and terminator. A suitable promoter would be taken from the gene for patatin in potato tubers. Advantageously any of the other starch degrading enzymes mentioned above could also be used instead of the ct β-amylase.

The inducible promoter of SEQ. ID. No. 8 could also be used in the construct if co-ordinated expression in the developing leaf and in the developing tuber were required, as the patatin promoter is also sucrose inducible (Rocha-Sosa et al (1989). Similarly, the sequence for the chloroplast targeting polypeptide of SEQ. ID. No. 1 could also be used with any other gene which lacked its own targeting sequence and which was required to be directed to plastids.

The above examples serve to illustrate the possible benefits of using the present invention. One skilled in the art will recognise that the combination of genes and the plants to which the invention could be applied is considerable.

Gene combinations preferably will include ct β-amylase with one or more of the genes for sucrose synthase, ADPG pyrophosphorylase, starch synthase, branching enzyme, α-amylase, isoamylase, non-plastidic β-amylase, α-glucosidase, starch phosphorylase and disproportionating enzyme, the sequences of which are known to the skilled man. Alternatively, the targeting sequence from ct β-amylase may be used with one or more of the above genes.

The list of plants which could be transformed preferably include potato, wheat, maize, barley, tomato, rice, pea, soybean, peanut, cassava, yam, banana and tobacco.

The invention will now be described, by way of example, with reference to an embodiment for isolation of the cDNA for ct β-amylase from *Arabidopsis thaliana* and for incorporating the cDNA into tobacco and potato plants. Examples are also given on the stimulus responsive promoter and its activity in transgenic plants.

In order that the invention may be readily carried into effect reference will now be made, by way of example, to the following diagrammatic drawings in which;

FIG. 1 shows the results of radiolabelled in vitro import translation products sampled on SDS-PAGE gel followed by fluorography. Legend: Molecular weight markers (lane M); translation products (lane Tr); chloroplasts reisolated and thermolysin-treated after import incubation (lane C); stromal fraction (lane S); washed thylakoids (lane T); thermolysin-treated thylakoids (lane tT); inner envelope fraction (lane I); outer envelope fraction (lane O). Putative precursor (P), intermediate (I) and mature (M) forms of β-amylase respectively. KiloDaltons (K);

FIG. 2 shows the effect of light and the effect of light and sugars on the expression of ct β-amylase transcript in *Arabidopsis thaliana* seedlings. FIG. 2a shows Northern blot analysis of total RNAs of 5-week old Arabidopsis plants grown in soil and exposed to 2 days continuous light (L), 2 days continuous darkness (D), 2 followed by 3 days of continuous light (LL) or 2 days of darkness followed by 3 days of continuous light (DL). FIG. 2b shows Northern blot analysis of total RNAs of 5-week old Arabidopsis plants, grown in vitro, which were transferred either into water and exposed to 3 days continuous light (WL); or into 5% sucrose and exposed to 3 days of darkness (SD) or 3 days of continuous light (SL); or into 5% glucose and exposed to 3 days of darkness (GD) or 3 days of continuous light (GL). Northern blots were hybridised with a radiolabelled ct-Bmy CDNA insert and autoradiographed (upper panels). The corresponding ethidium bromide-stained formaldehyde-agarose gels are shown in the bottom panels;

FIG. 3 shows the diagrammatic representation of the T-DNA of the chimaeric ct β-amylase promoter-GUS genes constructed in Example 3 below, in which NosP represents the nopaline synthase promoter; NosT represents the nopaline synthase terminator; BR is the right border inverted repeat and BL is the left border inverted repeat of the T-DNA of pBI101; NPTII represents the neomycin phosphotransferase II coding sequence; GUS represents the β-glucuronidase coding sequence. ct β-amylase promoter fragments are represented by hatched rectangles; the PCR amplified Xho I-Bam HI bridging fragments are represented by black rectangles;

Figure 6:
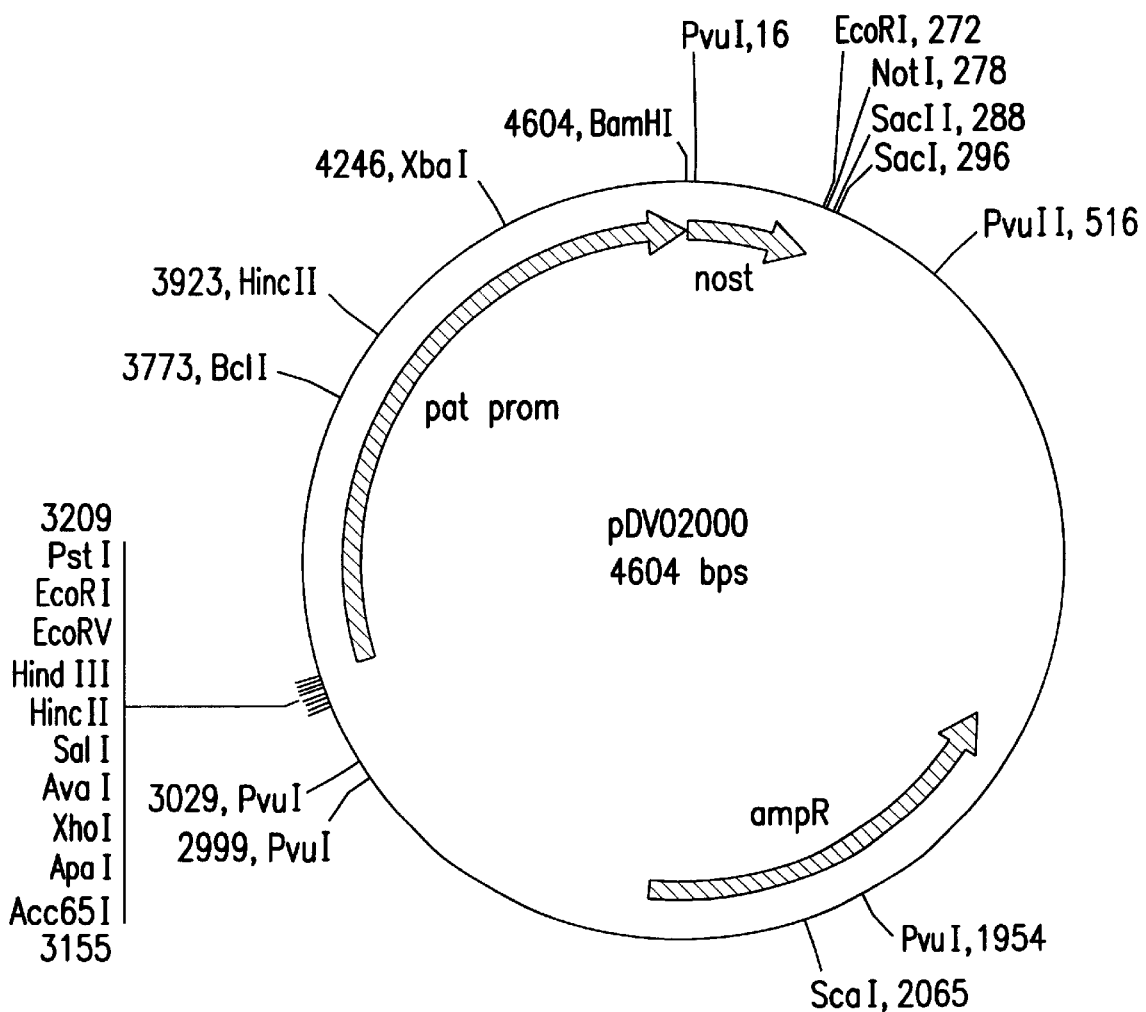
FIG. 6 shows the plasmid map of donator vector pDV02000.
Figure 7:
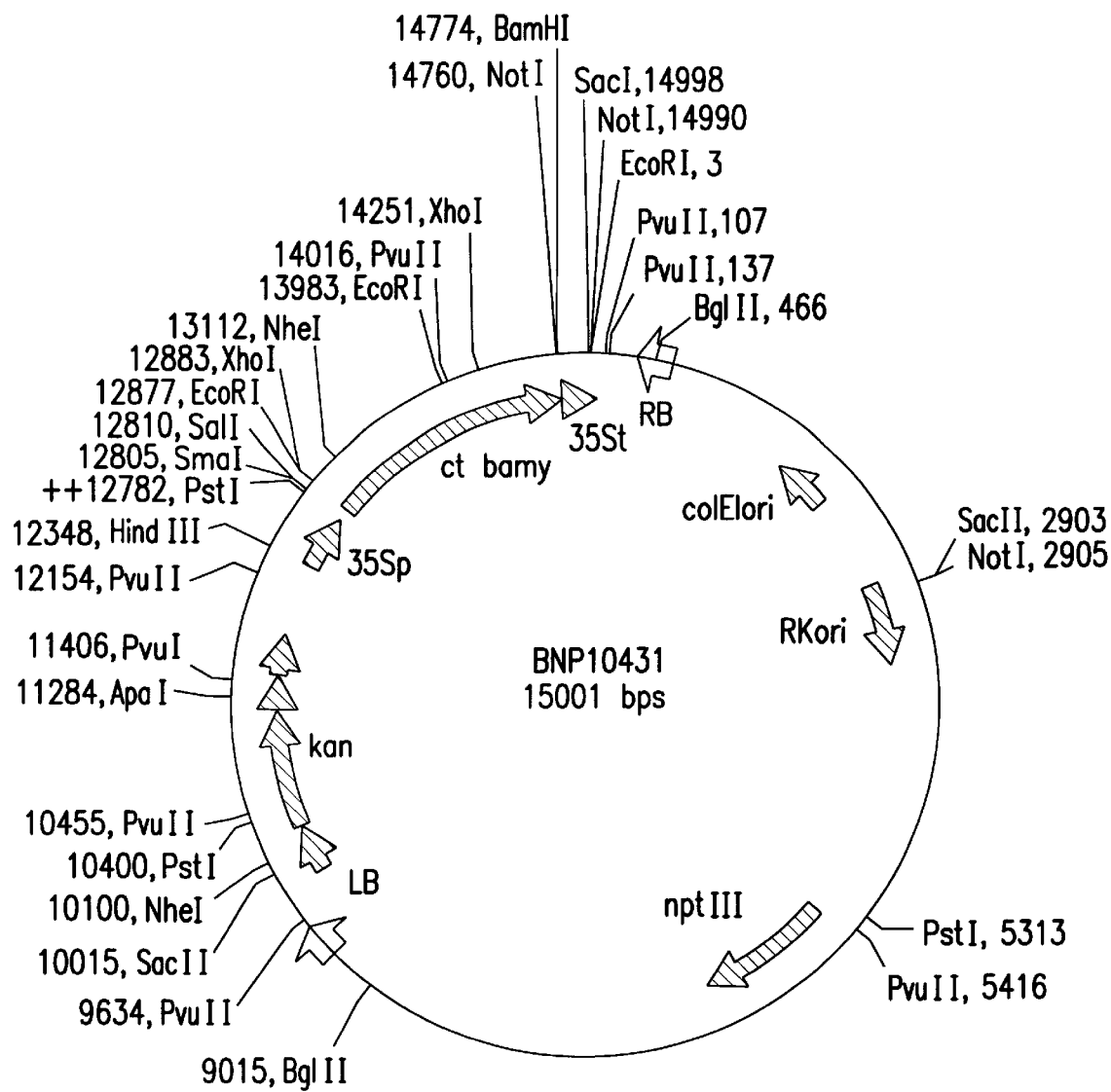
Figure 8:
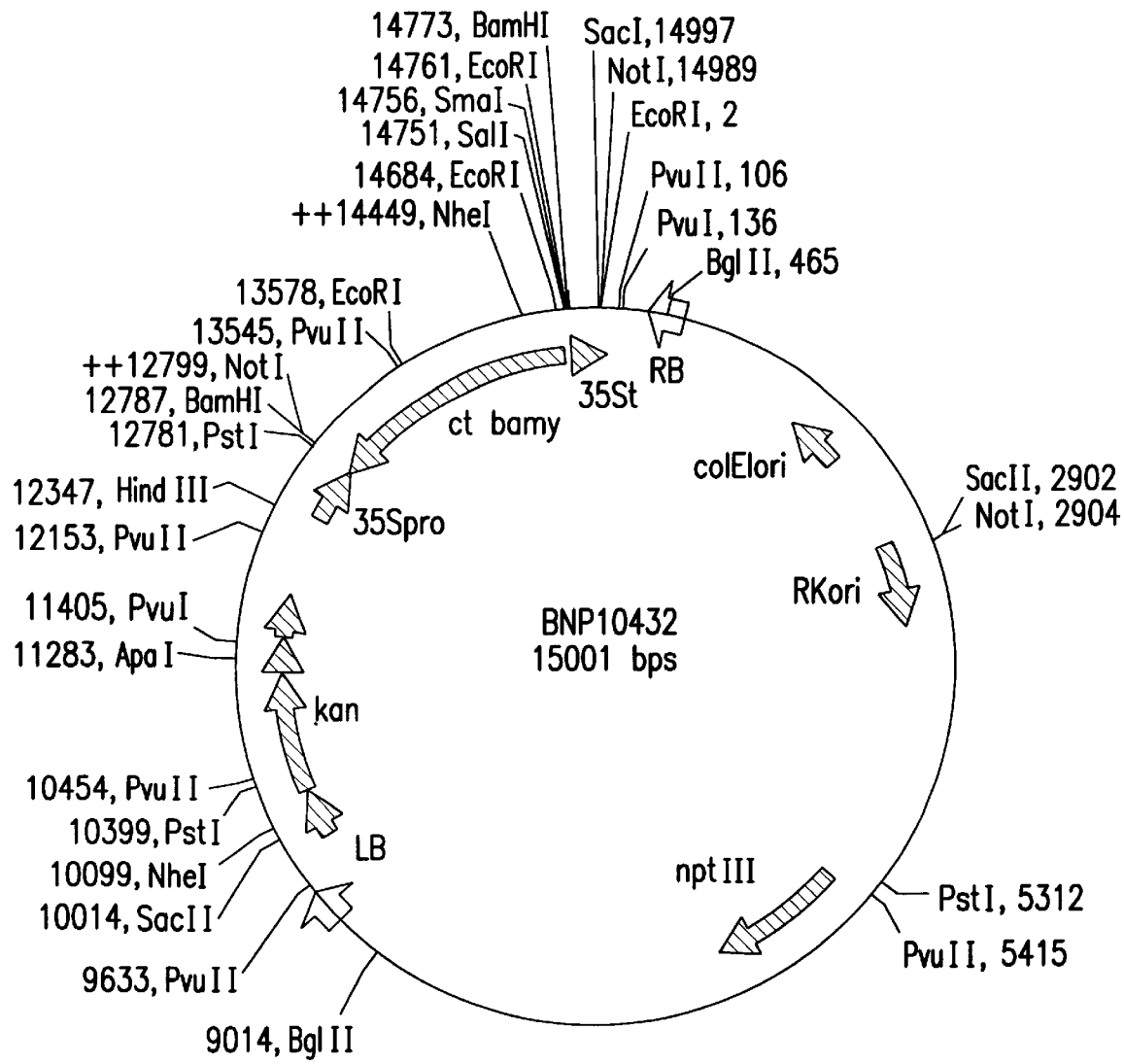
Figure 9:
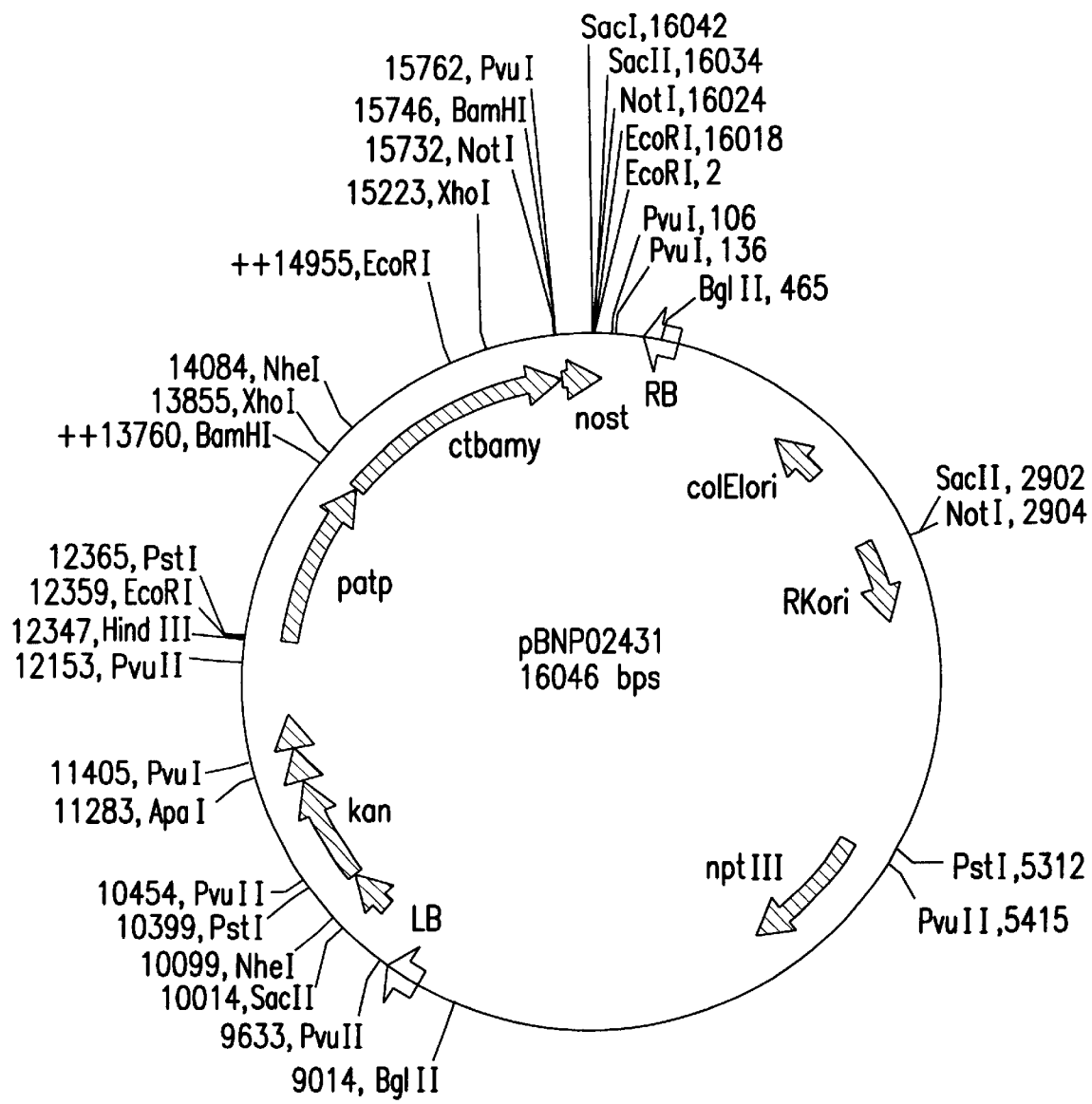
Figure 10:
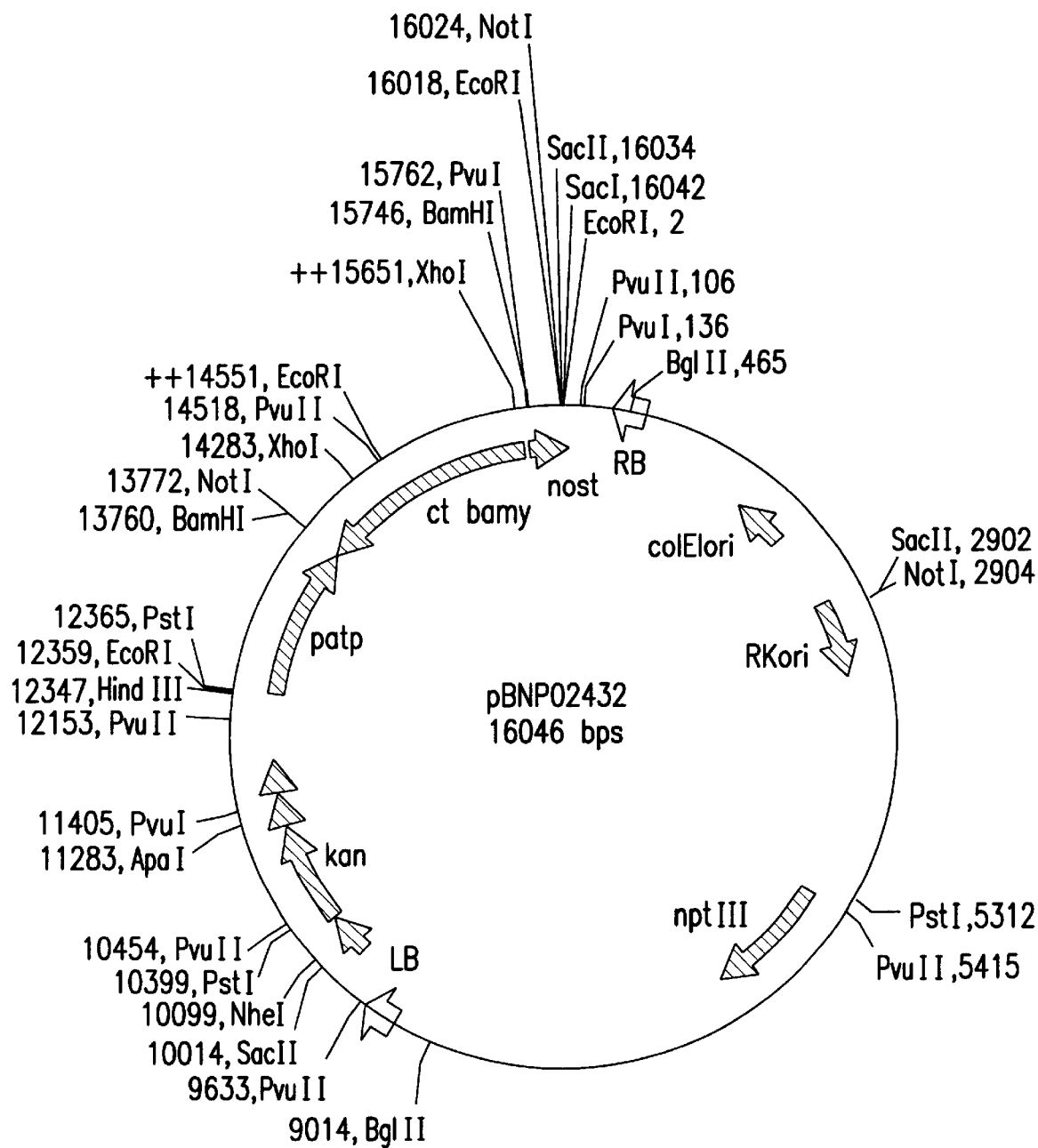

FIG. 7 shows the plasmid map of binary plasmid pBNP10431 where 35Sp represents the CaMV 35S promoter, ct bamy represents the full length ct β-amylase cDNA, 35St represents the CaMV 35S terminator, RB represents the right border of the binary vector pBinPlus, colElori represents the colE1 origin bacterial replication, RKori represents the oriV origin of replication of the RK2 plasmid, nptIII represents the neomycin phosphotransferase gene for bacterial resistance to kanamycin, LB represents the left border sequence of the binary vector, and kan represents the plant neomycin phosphotransferase recombinant gene required for plant resistance to kanamycin;

FIG. 8 shows the plasmid map of binary plasmid pBNP10432 where abbreviations are as for FIG. 7;

FIG. 9 shows the plasmid map of binary plasmid pBNP02431 where abbreviations are as for FIG. 7 except that patp represents the patatin class I promoter from vector pDV02000 in FIG. 6 and nost represents the nopaline synthase terminator; and FIG. 10 shows the plasmid map of binary plasmid pBNP02432 where abbreviations are as for FIG. 9.

In the sequence listing:

SEQ. ID. No. 1 is the nucleic acid capable of targeting a coding sequence to a plant plastid, particularly a chloroplast;

SEQ. ID. No. 2 is the nucleic acid which encodes β-amylase;

SEQ. ID. No. 3 is the complete sequence of chloroplast targeted (ct) α-amylase;

SEQ. ID. Nos. 4 and 5 are primers used in the amplification process of Example 3;

SEQ. ID. Nos. 6 and 7 are primers used in the amplification process of Example 4;

SEQ.ID. NO. 8 is the nucleic acid which is stimulus responsive, particularly to light and/or sugar.

SEQ. ID. NO. 9 is the predicted amino acid sequence of the nucleic acid found in SEQ. ID. NO. 1.

SEQ. ID. NO. 10 is the predicted amino acid sequence of the nucleic acid found in SEQ. ID. NO. 2.

SEQ. ID. NO. 11 is the predicted amino acid sequence of the nucleic acid found in SEQ. ID. NO. 3.

EXAMPLE 1

Isolation and Characterisation of *Arabidopsis thaliana* Chloroplast Targeted β-amylase Sequencing of CDNA Insert in pBmy81

A BLASTN database search of the nucleotide sequence of a 37 kb Arabidopsis chromosome IV DNA fragment in cosmid G16599 (Bevan et al., 1998) revealed the presence of a gene sharing significant homology with the extrachloroplastic β-amylase of Arabidopsis, barley maize rice soybean and rice. The search also identified several 3' terminal EST sequences, one of which, EST 81E10T7 (Newman et al., 1995), hereafter referred to as pBmy81, was identical over approximately 300 nucleotides. Clone EST 81E1OT7 was supplied by the Arabidopsis Biological Resource Center (ABRC) DNA Stock Center (Ohio State University, USA). A nested set of Bal3 deletion subclones, spanning the cDNA insert in pBmy81, were used as DNA templates in double stranded PCR cycle sequencing reactions using fluorescent dye-labelled universal primers. Sequencing reactions were analysed on an Applied Biosystems Model 373A automated sequencer. The nucleotide sequence of the CDNA insert in pBmy81 is shown in SEQ. ID No. 3. The construct pBmy81 was deposited by Advanced Technologies (Cambridge) Limited of 210 Cambridge Science Park, Cambridge CB4 4WA under the Budapest Treaty on the International Recognition of the Deposit of Micro-Organisms for the purposes of Patent Procedure at the National Collection of Industrial and Marine Bacteria (NCIMB), 23 St. Machar Street, Aberdeen Scotland on Aug. 4, 1998 under Accession No. NCIMB 40964.

Identification of a Putative Chloroplast Targeting Signal

The pBmy81 cDNA insert comprises 36 untranslated nucleotides at the 5' end, an open reading frame (ORF) that encodes a protein of 548 amino acids and a 3' untranslated region (UTR) of 232 bp. The protein encoded by the pBmy81 cDNA insert has a predicted molecular weight of 61 kDa and shares high amino acid similarity with plant extrachloroplastic β-amylases from maize, rice, barley, soybean and sweet potato. However, the protein encoded by pBmy81 differs from all other β-amylases reported so far in that it contains a unique N-terminal extension possessing the characteristics of a chloroplast targeting signal i.e. a high content of serine (16%), threonine (10%) and positively charged amino acid residues (15%) (Baier and Dietz, 1997). Three domains which are distinguishing features of chloroplast targeting signals (Schatz and Dobberstein, 1996) were identified in the signal sequence: an uncharged amino-terminal domain; a central domain rich in hydroxylated amino acids; and a carboxy-terminal domain with the potential to form an amphiphilic β-strand.

CDNA Insert in pBmy81 Encodes a Chloroplast Targeted α-amylase

Intact chloroplasts were isolated from 50–60 g of pea shoots (*Pisum sativum* L. var Feltham First) using Percoll step-gradients. Plant material was grown and chloroplasts isolated according to the method of Mould and Gray (1997a).

The pBmy81 plasmid was linearised by restriction digestion with NotI and was transcribed in vitro using T7 RNA polymerase. Radiolabelled precursor protein was synthesised in a wheat germ translation system, including $^{35}$S-methionine and $^{35}$S-cysteine from transcripts of the pBmy81 cDNA essentially as described by Mould and Gray (1997b).

Figure 1:
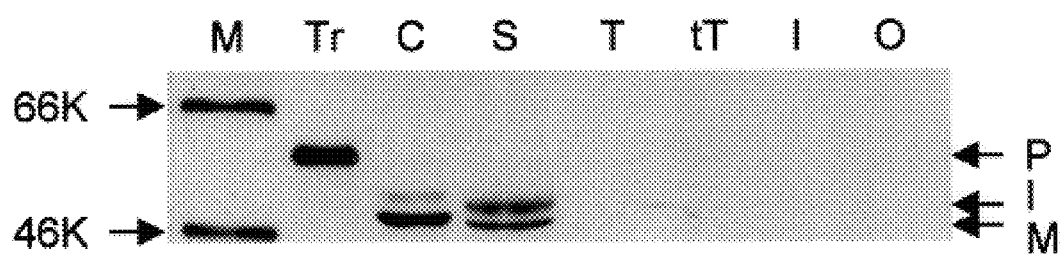

Import of radiolabelled in vitro translation products was performed as described by Mould and Gray (1997b). After the import incubation, intact chloroplasts were treated with thermolysin (0.2 mg/ml final concentration in import buffer) for 30 min on ice and then the protease reaction was stopped by the addition of EDTA to 50mM in import buffer. Chloroplasts were re-isolated through a cushion of 40% Percoll in import buffer and then washed in import buffer (Mould and Gray, 1997b). An aliquot (1/10) of the thermolysin-treated chloroplast sample was taken for analysis and the remainder was fractionated essentially as described by Schnell and Blobel (1993). Samples of thermolysin-treated chloroplasts, stromal fraction, thylakoids and thermolysin-treated thylakoids were quantified by SDS-PAGE followed by coomasie blue staining and scanning densitometry of stained protein bands (subunits of ribulose bisphosphate carboxylase and light harvesting complex proteins were used as standards). Equivalent amounts of these fractions (approximately equal to 2% of the chloroplasts recovered from the Percoll gradient), and 505 of the inner and outer envelope fractions recovered, were analysed by electrophoresis on a 10% polyacrylamide gel in the presence of SDS, followed by fluorography. Results (FIG. 1) show that the major translation product (lane Tr) was approximately 58 kDa. When isolated, intact pea chloroplasts were incubated with the radiolabelled protein in the presence of ATP, polypeptides of approximately 50 kDa and 48 kDa were generated (lane C). The resistance of these polypeptides to degradation by exogenously added thermolysin, indicates that they are products of radiolabelled protein import. Fractionation of the intact thermolysin-treated chloroplasts into stroma, washed thylakoids, thermolysin-treated thylakoids, inner envelopes and outer envelopes, demonstrated that the two radiolabelled polypeptides were located in the stromal fraction.

EXAMPLE 2

Sucrose and Light Induction of Arabidopsis Thaliana Ct β-amylase Gene.

To demonstrate the induction of ct b-amylase in light *Arabidopsis thaliana* ecotype Landsberg plants were grown in the green house under an 18 hour light, 6 hour dark regime at 18° C. After 5 weeks, two trays of seedlings were transferred to complete darkness and two trays of seedlings were grown in continuous light. After two days, one tray of dark-adapted seedlings and a tray of light grown seedlings were used for isolation of total RNAs, and the second tray of each were exposed to a further 3 days of continuous light.

For combined sucrose-light-dark treatments, seeds of Landsberg ecotype were surface sterilised, placed on MS agar medium containing 1% sucrose and grown in a culture room with an 18 hour light, 6 hour dark regime. Five week old seedlings were transferred onto sterilised distilled water or a 5% solution of sucrose or glucose in water. The seedlings were maintained either in continuous light or darkness for three days. Total RNAs were prepared from seedlings of each test and were analysed by northern blot analysis as described by Eggermont et al. (1996). Northerns were probed with the gel-purified cDNA insert in pBmy81 following random labelling with $^{32}$P-dCTP as described by Feinberg and Vogelstein (1983).

Figure 2A:
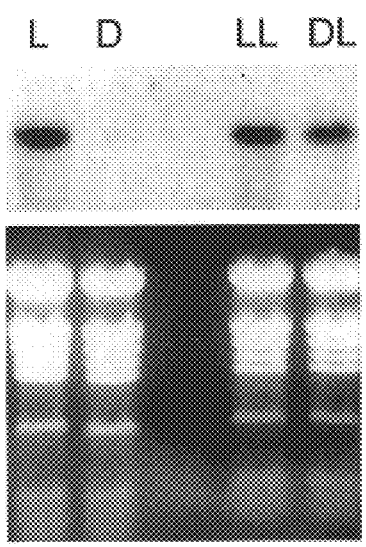

The results shown in FIG. 2A indicate that the ct β-amylase genetranscript is inducible due to light.

Figure 2B:
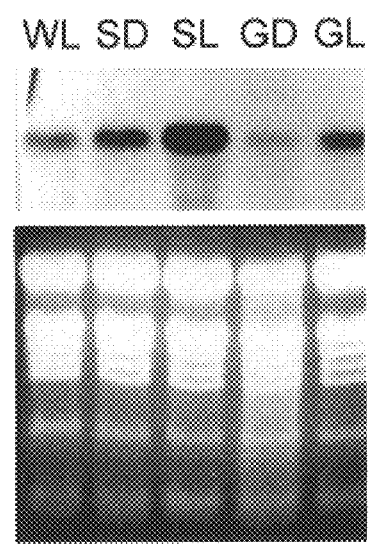

The results shown in FIG. 2B indicate that the ct β-amylase transcript is induced in the dark with 5% sucrose and to a lesser extent with 5% glucose. This induction is enhanced further in the light in the presence of the sugars. These results show that the effect of light and sugars are independent of each other.

EXAMPLE 3
Construction of ct β-amylase Promoter-GUS Fusions

Promoter fragments were isolated from the ct β-amylase gene located in cosmid G16599 (Bevan et al., 1998) by restriction enzyme digestion. Convenient restriction sites in the promoter were Hind III at nucleotide position –1662 bp (starting at 19179 bp on the minus strand of SEQ. ID. No. 8), Sal I at –1127 bp and Pst I at –371 bp and an Xho I site located at position +21 bp downstream of the ct β-amylase initiating methionine were used to isolate three different lengths of promoter plus transit peptide sequence (the A of the translation initiation methionine ATG is numbered +1).

A 294 bp (SEQ. ID. No. 1) fragment of the ct β-amylase gene located in cosmid G16599 (Bevan et al., 1998) was amplified using the oligonucleotide primers:
SEQ. ID. No. 4
P1: (5'-AAT TCC TCG AGT TCT CTT ATC-3') and
SEQ. ID. No. 5
P2: (5'-cgg gAT CCC TGA CAT TGT TAC-3').

In primer P1, the underlined bases refers to the Xho I site located at position +21 bp; in primer P2 the bases in lower case refer to the nucleotides added in order to create a Bam HI site.

Figure 3:
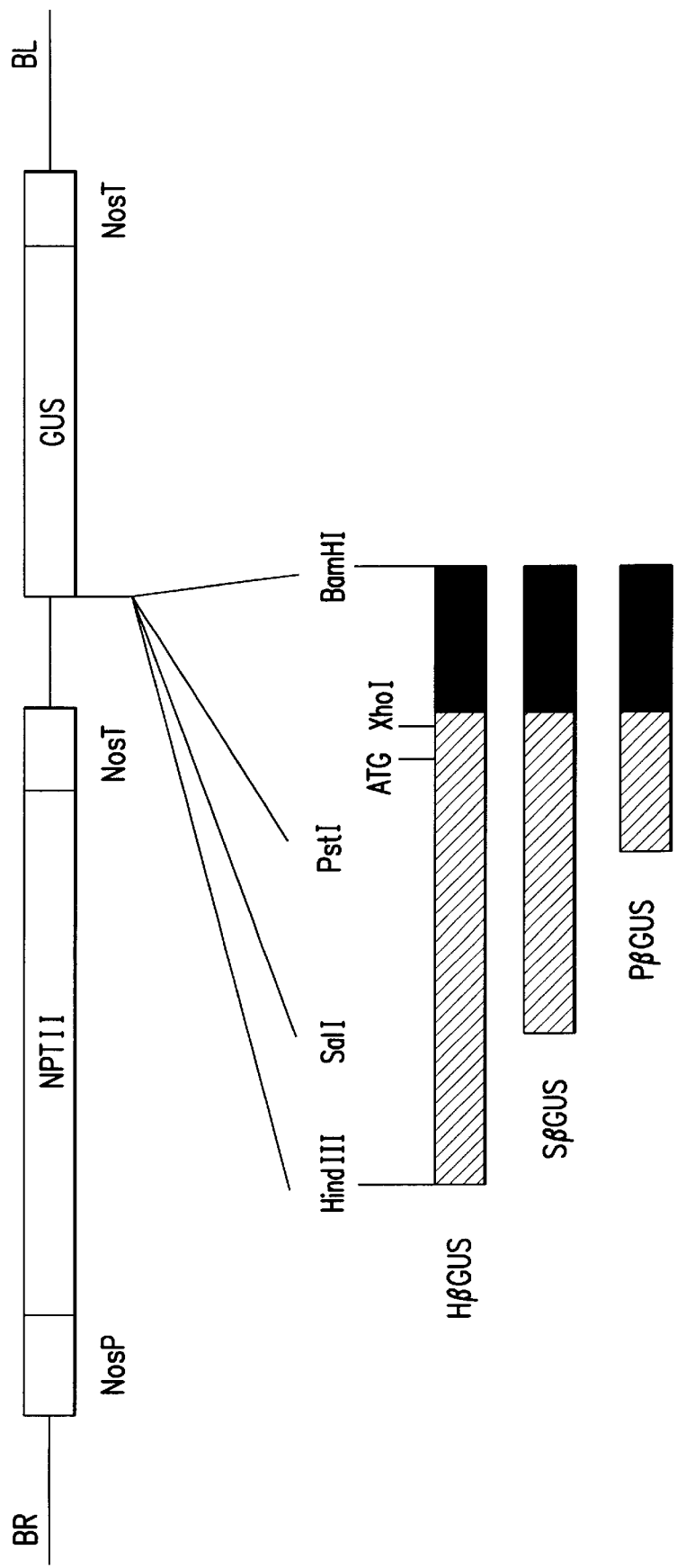

Chimaeric ct β-amylase promoter-GUS genes were created by triple ligation of the promoter fragment; the PCR bridging fragment digested with Xho I and Bam HI; and the GUS vector pBI101 (Jefferson et al., 1987) digested with Hind III-Bam HI, Sal I-Bam HI or Pst I-Bam HI (FIG. 3). Constructs were termed HβGUS, SβGUS and PβGUS respectively.

The chimaeric gene constructs were transferred to *Agrobacterium tumefaciens* LBA4404 by triparental mating (Bevan, 1984) and introduced into *Nicotiana tabacum* var Samsun by the leaf disk transformation method (Horsch et al., 1985).

EXAMPLE 3A
Sucrose and Light Induction of Chimaeric *Arabidopsis Thaliana* ct β-amylase Promoter-GUS Gene in Tobacco Seedlings.

Figure 4:
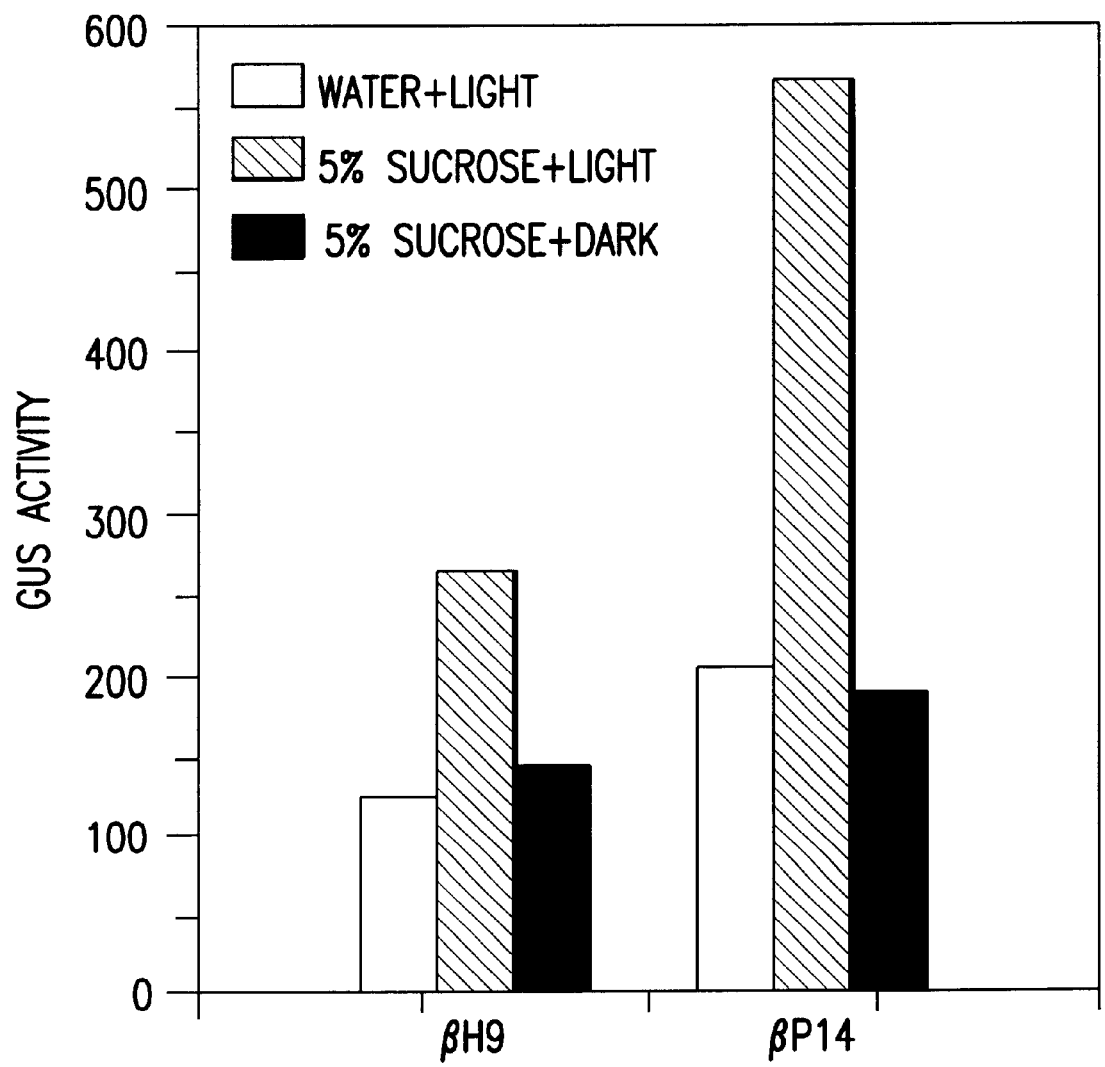
FIG. 4 shows the effect of light and sucrose on the GUS activity expressed from a ct Bmy promoter-GUS chimaeric gene in tobacco seedlings.

Plants containing the HβGUS and PβGUS constructs expressed high levels of GUS activity and F1 seedling progeny of the lines were used to investigate light and sucrose inducible expression of the chimaeric genes. F1 tobacco seeds were surface sterilised, placed on MS agar medium containing 1% sucrose and grown in a culture room with an 18 hour light, 6 hour dark regime. Two to three week old seedlings were transferred onto a 5% sucrose solution or onto distilled water and maintained either in continuous light or darkness for three days. Total protein extracts from pools of 10 to 14 seedlings were analysed for GUS activity using the fluorogenic substrate 4-methylumbelliferyl-glucuronide (4-MUG) as described by Jefferson et al. (1987). With both constructs, the level of GUS activity in seedlings exposed to continuous light in the absence of sucrose was similar to the levels of GUS activity in seedlings exposed to sucrose in the absence of light (FIG. 4). However, exposure of seedlings to both continuous light and sucrose increased levels of GUS activity by approximately two to three fold. These results are broadly in agreement with the results from the experiments with the ct b-amylase gene itself which showed that light inducibility and sucrose inducibility are independent processes.

Histochemical staining for GUS showed that activity was detected in the cotyledons of two week old seedlings and little or no activity in the first true leaves or in the stems and roots. In four week old seedlings, additional GUS activity was shown throughout the first true leaves and also in the stems. GUS staining was particularly associated with chloroplast-rich parenchyma (chlorenchyma) cells located between the xylem rays and between xylem and the bundles of phloem that constitute the internal phloem in stems.

EXAMPLE 4
Construction of ct β-amylase Plasmids for Use in Transformation of Tobacco and Potato Leaves Site-directed mutagenesis was used to convert the Kpn I site located at position 2302 bp of the pBmy81 plasmid to a Bam HI site. Oligonucleotide primers
SEQ. ID. No. 6
P3: (5'-GCT GGT ACG CCT GCA GGA TCC GGT CCG GAA TTC CC-3') and
SEQ. ID. No. 7
P4: (5'-GGG AAT TCC GGA CCG GAT CCT GCA GGC GTA CCA GC-3')
were designed and used with the Quick Change site-directed mutagenesis kit (Promega). Protocol was as outlined by the manufacturer.

Figure 5:
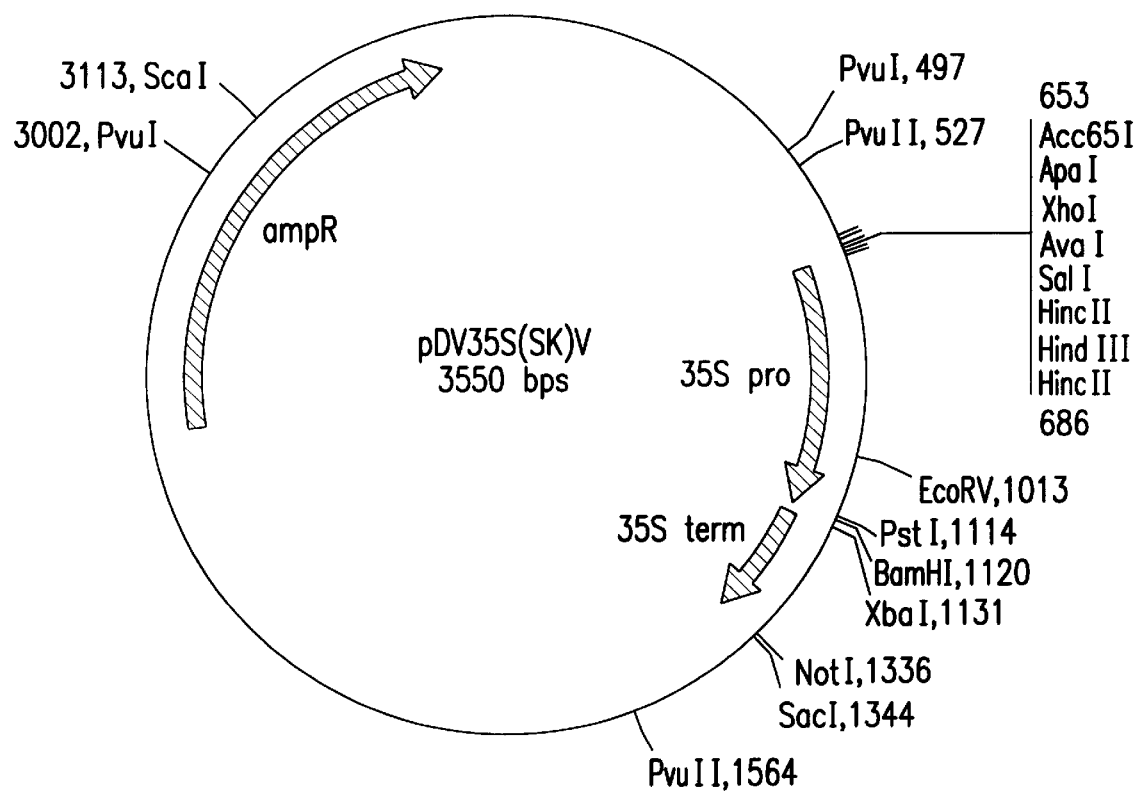
FIG. 5 shows the plasmid map of donator vector pDV35S (SK)V.

The full length ct β-amylase coding sequence was excised from the mutated pBmy81 plasmid by cleavage with Bam HI and then purified with GeneClean (BIO 101). The Bam HI fragment was ligated into the Bam HI site of the donator vectors pDV35S(SK)V (see FIG. 5) and pDV02000 (see FIG. 6). pDV35S(SK)V consists of pBluescript (Stratagene) carrying a 35S CaMV promoter-35S terminator, similar constructs are known in the art (e.g. Odell et al., 1985). pDV02000 consists of pBluescript with a 1.4 kbp patatin promoter-nopaline synthase terminator. One skilled in the art could make similar constructs from known sequences (e.g. Liu et al., 1990). Plasmids with the coding sequence in both the sense and antisense orientation relative to the promoters were isolated, and the ct β-amylase chimaeric genes subcloned from the donator vectors into the binary vector pBinPlus (van Engelen et al., 1995). The plasmid maps are shown in FIGS. 7–10.

EXAMPLE 5
Transformation or Retransformation of Plants

Potato plants were transformed using the method of leaf disk cocultivation as essentially described by Horsch (1985). The binary vectors as described above were transferred to Agrobacterium tumefaciens LBA4404 using the method of electroporation, and cultures of said Agrobacteria used in transformation so that regenerated plants carry the chimaeric genes as described in Example 4.

The patatin promoter-ct α-amylase-nopaline synthase terminator chimaeric gene binary plasmid, can be used to transform a potato plant already carrying the chimaeric gene for E. coli ADPG-Ppase glgC16 by the methods of leaf disk cocultivation.

EXAMPLE 6
Construction of Plasmids with the Targeting Peptide of AT ct β-amylase The plastid targeting sequence of AT ct β-amylase is contained within a 294 bp fragment equivalent to SEQ. ID. No. 1. PCR amplification or restriction enzyme digestion can be used to isolate fragments of DNA from the plasmids described in Example 3, i.e. fragments will consist of the 35S CaMV promoter plus plastid targeting sequence or the patatin promoter plus the plastid targeting sequence. Chimaeric genes can be constructed by ligating coding sequences for proteins or enzymes as translational fusions with the transit peptide sequence. Translated proteins would be transported to the plastids to provide novel activities or to affect metabolic pathways.

REFERENCES

Ainsworth, C., Clark, J. and Balsdon, J. (1993). Plant. Mol. Biol., 22, 67–82.

Baier, M. and Dietz, K. J., (1997) Plant J. 12, 179–190

Bevan, M. W. (1984) Nucl. Acids. Res., 12, 8711–8721

Bevan, M. W. et al. (1998). Nature, 391, 485–488.

Chan, M T., Chao, Y C. and Yu, S M. (1994). J. Biol. Chem., 269, 17635–17641.

Chen, M H., Liu, L F., Chen, Y R., Wu, H K. and Yu, S M. (1994). Plant J., 6, 625–636.

Daussant, J., Zbaszyniak, B., Sadowski, J. and Wiatroszak, I. (1981). Planta, 151, 176–179.

Denyer, K., Clarke, B., Hylton, C., Tatge, H. and Smith, A. M. (1996). Plant J., 10, 1135–1143.

Duwenig, E., Steup, M., Willmitzer, L. and Kossmann, J. (1997). Plant J., 12, 323–333.

Eggermont, K., Goderis, I. J. and Broekaert, W. F. (1996). Plant Mol. Biol. Rep. 14, 273–279.

Feinberg, A. P. and Vogelstein, B. (1983). Anal. Biochem. 132, 6–13.

Gelvin, S. B. and Schilperoort, R. A. (1995). Plant Molecular Biology Manual. $2^{nd}$ edition. Kluwer Academic Publishers, The Netherlands.

Hildebrand, D. F. and Hymowitz, T. (1981). Physiol. Plant., 53, 429–434.

Horsch, R. B., Fry, J. E., Hoffman, N. L., Eichholtz, D., Rogers, S. G. and Swaley, R. T. (1985) Science, 227. 1229–1231.

Hylton, C. M., Denyer, K., Keeling, P. L., Chang, M T. and Smith, A. M. (1995). Planta, 198, 230–237.

Innes, M. A., Gelfand, D. H., Sninsky, J. J. and White, T. J. (1990). PCR Protocols. Publisher: Academic Press.

James, M. G., Robertson, D. S. and Myers, A. M. (1995). Plant Cell, 7, 417–429.

Jefferson, R. A., Kavanagh, T. A. and Bevan, M. W. (1987) EMBO, J. 6. 3901–3907.

Kakefuda, G., Duke, S. H. and Hostak, M. H. (1986). Planta, 168, 175–182.

Klosgen, R. B. and Weil, J. H. (1991) Mol. Gen. Genet., 225, 297–304

Li, B., Servaites, J. C. and Geiger, D. R. (1992). Plant Physiol., 98, 1277–1284.

Liu, X. J., Prat, S., Willmitzer, L. and Frommer, W. B. (1990) Mol. Gen. Genet., 223, 401–406.

Mita, S., Suzuki-Fujii, K. and Nakamura, K. (1995) Plant Physiol. 107,895–904.

Mita, S., Murano, N., Akaike, M. and Nakamura, K. (1997). Plant J., 11, 841–851.

Mould, R. M. and Gray, J. C. (1997a). In Cell Biology: A Laboratory Handbook, second edition, Volume 2. (Cells, J. E. ed). New York: Academic Press, pp. 81–86.

Mould, R. M. and Gray, J. C. (1997b). In Cell Biology: A Laboratory Handbook, second edition, Volume 2. (Cells, J. E. ed). New York: Academic Press, pp. 286–292.

Nakamura, K., Ohto, M., Yoshida, N. and Nakamura, K. (1991). Plant Physiol., 96, 902–909.

Neuhaus, H. E., Henrichs, G. and Schiebe, R. (1995). Planta, 194, 454–460.

Newman, T. et al. (1994). Plant Physiol., 106, 1241–1255.

Nielson, T. H., Deiting, U. and Stitt, M. (1997). Plant Physiol., 113, 503–510.

Odell, J. T. Nagy, F. and Chua, N. H. (1985) Nature, 313, 810–812.

Peavey, D. G., Steup, M. and Gibbs, M. (1977). Plant Physiol., 60, 305–308.

Pwee, K-H. and Gray, J. C. (1993) Plant J. 3, 437–449.

Rocha-Sosa, M., Sonnewald, U., Frommer, W., Stratmann, M.,

Schell, J. and Willmitzer, L. (1989) EMBO, 8, 23–29.

Sambrook, J., Fritsch, E. F. and Maniatis, T. (1989). Molecular Cloning. Publisher: Cold Spring Harbour.

Schatz, G. and Dobberstein, B. (1996). Science, 271, 1519–1526.

Schnell, D. J. and Blobel, G. (1993). J. Cell. Biol., 120, 103–115.

Sonnewald, U., Basner, A., Greve, B. and Steup, M. (1995). Plant. Mol. Biol., 27, 567–576

Sweetlove, L. J., Burrell, M. M. and ap Rees, T. (1996). Biochem. J., 320, 493–498.

Thomson, W. W. and Whatley, J. M. (1980) Ann. Rev. Plant Physiol. 31, 375–394.

van Engelen, F. A., Molthoff, J. W., Conner, A. J., Nap, J-P., Pereira, A. and Stiekema, W. J. (1995). Transgenic Res. 4, 288–290.

van der Leij, F. R., Visser, R. G. F., Ponstein, A. S., Jacobsen, E. and Feenstra, W. J. (1991). Mol. Gen. Genet., 228, 240–248.

Wang, S M., Lue, W L. and Chen, J. (1996). Plant Mol. Biol., 31, 975–982.

Wang, S M., Lue, W L., Huang, H W. and Chen, J. (1997). Plant Physiol., 113, 403–409.

What is claimed is:

1. A chimeric nucleic acid molecule comprising a first nucleic acid sequence which consists of the nucleotide sequence from position 37 to position 1683 of SEQ ID NO:3 linked to a second heterologous nucleic acid sequence.

2. A method for producing a polypeptide comprising
   (i) providing a cell comprising a chimeric nucleic acid molecule, said chimeric nucleic acid molecule comprising a first nucleic acid sequence that encodes an amino acid sequence which is encoded by the nucleotide sequence from position 37 to position 1683 of SEQ ID NO:3, and is operably linked to a second nucleic acid sequence that regulates the expression of the first nucleic acid sequence in the cell; and
   (ii) culturing the cell under conditions in which the first nucleic acid sequence is expressed thereby producing the polypeptide.

3. A method for producing a chimeric polypeptide comprising
   (i) providing a cell comprising a chimeric nucleic acid molecule that encodes a chimeric polypeptide, wherein said chimeric nucleic acid molecule comprises a first nucleic acid, of SEQ ID NO:2, wherein said first nucleic acid sequence is linked to a second nucleic acid sequence; and
   (ii) culturing the cell under conditions in which the chimeric nucleic acid molecule is expressed thereby producing the chimeric polypeptide.

4. The method according to any one of claim 2 or 3, wherein the chimeric nucleic acid molecule comprises a promoter selected from the group consisting of a full cauliflower mosaic virus 35S promoter, a truncated cauliflower mosaic virus 35S promoter, a rubisco promoter, a pea plastocyanin promoter, a nopaline synthase promoter, a chlorophyll a/b binding promoter, a high molecular weight glutenin promoter, a α-gliadin promoter, a β-gliadin promoter, a hordein promoter, and a patatin promoter.

5. An isolated nucleic acid molecule comprising (a) a nucleotide sequence that encodes a polypeptide consisting essentially of the amino acid sequence encoded by nucleotides 37 to 1683 of SEQ ID NO: 3; (b) the nucleotide sequence of SEQ ID NO: 3; (c) the complement of (a); or (d) the complement of (b).

6. An isolated nucleic acid molecule comprising (a) a nucleotide sequence that encodes a polypeptide consisting essentially of the amino acid sequence encoded by nucleotides 1 to 1389 of SEQ ID NO:2; (b) the nucleotide sequence of SEQ ID NO:2; (c) the complement of (a); or (d) the complement of (b).

7. A method of increasing the activity of β-amylase in a plant cell comprising the steps of introducing into the plant cell a nucleic acid molecule comprising the nucleic acid sequence of SEQ ID NO: 3; and expressing the nucleic acid sequence, such that the activity of β-amylase is increased relative to a plant cell without the nucleic acid molecule.

8. A method of increasing the activity of β-amylase in a plant cell comprising the steps of introducing into the plant cell a chimeric gene comprising a first nucleic acid molecule comprising the nucleic acid sequence of SEQ ID NO: 2 operably linked to a second nucleic acid sequence; and expressing the chimeric gene such that the activity of β-amylase is increased relative to a plant cell without the chimeric gene.

9. The method according to claim 7 or 8, wherein said plant cell is regenerated into a plant.

10. The method according to claim 7 or 8, wherein the nucleic acid molecule further comprises a promoter selected from the group consisting of a full cauliflower mosaic virus 35S promoter, a truncated cauliflower mosaic virus 35S promoter, a rubisco promoter, a pea plastocyanin promoter, a nopaline synthase promoter, a chlorophyll a/b binding promoter, a high molecular weight glutenin promoter, a α-gliadin promoter, a β-gliadin promoter, a hordein promoter, and a patatin promoter.

11. A chimeric nucleic acid molecule comprising a first nucleic acid sequence which consists of the nucleotide sequence of SEQ ID NO:2 linked to a second heterologous nucleic acid sequence.

12. The chimeric nucleic acid molecule of any one of claim 1 or 11, wherein the chimeric nucleic acid molecule comprises a promoter selected from the group consisting of a full cauliflower mosaic virus 35S promoter, a truncated cauliflower mosaic virus 35S promoter, a rubisco promoter, a pea plastocyanin promoter, a nopaline synthase promoter, a chlorophyll a/b binding promoter, a high molecular weight glutenin promoter, a α-gliadin promoter, a β-gliadin promoter, a hordein promoter, and a patatin promoter.

13. The chimeric nucleic acid molecule of any one of claim 1, or 11 wherein the chimeric nucleic acid molecule sequence further comprises vector sequences.

14. A cultured cell which comprises the chimeric nucleic acid molecule of any one of claim 1, or 11.

15. The cultured cell of claim 14 wherein the cell is a prokaryotic cell or an eukaryotic cell.

16. The cultured cell of claim 14 wherein the cell is a plant cell.

17. A plant comprising the cultured cells of claim 14, or progeny thereof wherein the progeny comprises the chimeric nucleic and molecule.

18. The plant of claim 17, wherein the plant is a potato, wheat, maize, barley, tomato, rice, pea, soybean, peanut, cassava, yam, banana, or tobacco.

19. A seed of the plant of claim 17 wherein the seed compresses the chimeric nucleic acid molecule.

* * * * *